United States Patent
Khanna et al.

(10) Patent No.: US 11,020,391 B2
(45) Date of Patent: *Jun. 1, 2021

(54) CRMP2 SUMOYLATION INHIBITORS AND USES THEREOF

(71) Applicant: ARIZONA BOARD OF REGENTS ON BEHALF OF THE UNIVERSITY OF ARIZONA, Tucson, AZ (US)

(72) Inventors: May Khanna, Tucson, AZ (US); Rajesh Khanna, Tucson, AZ (US); Vijay Gokhale, Tucson, AZ (US); Reena Chawla, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/596,508

(22) Filed: Oct. 8, 2019

(65) Prior Publication Data

US 2020/0093822 A1 Mar. 26, 2020

Related U.S. Application Data

(63) Continuation of application No. 15/766,299, filed as application No. PCT/US2016/056051 on Oct. 7, 2016, now Pat. No. 10,441,586.

(60) Provisional application No. 62/238,182, filed on Oct. 7, 2015.

(51) Int. Cl.
| | |
|---|---|
| *A61K 31/496* | (2006.01) |
| *C07D 295/135* | (2006.01) |
| *A61K 31/495* | (2006.01) |
| *C07D 295/185* | (2006.01) |
| *C07D 405/12* | (2006.01) |
| *C07D 317/68* | (2006.01) |
| *A61K 31/452* | (2006.01) |
| *A61K 31/5377* | (2006.01) |
| *A61P 25/02* | (2006.01) |
| *A61K 31/4525* | (2006.01) |

(52) U.S. Cl.
CPC .......... *A61K 31/496* (2013.01); *A61K 31/452* (2013.01); *A61K 31/4525* (2013.01); *A61K 31/495* (2013.01); *A61K 31/5377* (2013.01); *A61P 25/02* (2018.01); *C07D 295/135* (2013.01); *C07D 295/185* (2013.01); *C07D 317/68* (2013.01); *C07D 405/12* (2013.01)

(58) Field of Classification Search
CPC ............... A61K 31/496; A61K 31/452; A61K 31/4525; A61K 31/495; A61K 31/5377; A61P 25/02; C07D 295/135; C07D 295/185; C07D 317/68; C07D 405/12
USPC ................................................. 514/235.8
See application file for complete search history.

(56) References Cited

U.S. PATENT DOCUMENTS

| | | | |
|---|---|---|---|
| 2,870,146 A | 1/1959 | Perron et al. | |
| 4,305,940 A | 12/1981 | Quadro | |
| 10,441,586 B2 * | 10/2019 | Khanna | ................ C07D 405/12 |
| 2011/0315662 A1 | 6/2011 | Finney et al. | |

FOREIGN PATENT DOCUMENTS

| | | |
|---|---|---|
| WO | WO 2005/040121 | 5/2005 |
| WO | WO 2009/049181 | 4/2009 |
| WO | WO 2009/049183 | 4/2009 |
| WO | 2011/051350 | 5/2011 |
| WO | WO 2012/027392 | 3/2012 |
| WO | WO 2012/053186 | 4/2012 |
| WO | WO 2014/151472 | 9/2014 |
| WO | WO 2015/119998 | 8/2015 |
| WO | WO 2015/134920 | 9/2015 |

OTHER PUBLICATIONS

International Search Report and Written Opinion, International Patent Application No. PCT/US2016/056051, dated Dec. 23, 2016.
PUBCHEM-CID-1086053, Create Date: Jul. 10, 2005, entire document, especially: Figure, p. 3.
Dustrude et al. "CRMP2 Protein SUMOylation Modulates NaV1.7 Channel Trafficking" JPC 2013. vol. 288(34), pp. 24316-24331.
PUBCHEM-CIPD-21634109, Create Date: Dec. 5, 2007, entire document, especially: Figure, p. 3.
Bujak et al., Discovery of TRAF-2 and NCK-interacting kinase (TNIK) inhibitors by ligandbased virtual screening methods, Med. Chem. Commun. vol. 6 No. 8, 1564-1572, Jun. 24, 2015.
CAS Registry # 425615-79-8, N-[4-(4-acetyl-1-piperazinyl)phenyl]-3-methoxybenzamide,Source of Registration: ChemBridge Corporation, Entered in STN on Jun. 5, 2002.
CAS Registry #577998-64-2, 3-(1-methylethoxy)-N-[4-(4-methyl-1-piperazinyl)phenyl]-benzamide, Source of Registration: Ambinter, Entered in STN Sep. 3, 2003.
CAS REG No. 689746-85-8, STN Entry Date: Jun. 6, 2004; Benzamide, 3,5-dimethoxy-N-[4-(4-methyl-1-piperazinyl)phenyl]-.
CAS REG No. 797028-94-5, STN Entry Date: Dec. 14, 2004; 1,3-Benzodioxole-5-carboxamide, N-[4-(4-methyl-1-piperazinyl)phenyl]-.

(Continued)

*Primary Examiner* — Kristin A Vajda
(74) *Attorney, Agent, or Firm* — Casimir Jones, S.C.; Robert A. Goetz

(57) ABSTRACT

The present invention provides compounds that can modulate the amount of Nav1.7 protein, a key protein in pain signaling, that is present in the cellular surface and methods for using such compounds. In particular, compounds of the invention modulate the amount of Nav1.7 protein on the cellular surface by modulating SUMOylation of CRMP2. Thus, compounds of the invention can be used to treat various clinical conditions associated with the presence and/or activation of Nav1.7 protein on the cellular surface and/or SUMOylation of CRMP2.

11 Claims, 8 Drawing Sheets

(56) References Cited

OTHER PUBLICATIONS

Chattopadhyay, C. et al. Continuous delta-opioid receptor activation reduces neuronal voltage-gated sodium channel (NaV1.7) levels through activation of protein kinase C in painful diabetic neuropathy. J Neurosci. Jun. 25, 2008;28(26):6652-8.
Supplementary European Search Report, EP Patent Application No. 16854447.6, dated Jul. 16, 2019.
PUBCHEM SID: 844767, Deposited: Jun. 4, 2005, 5 pages.

* cited by examiner

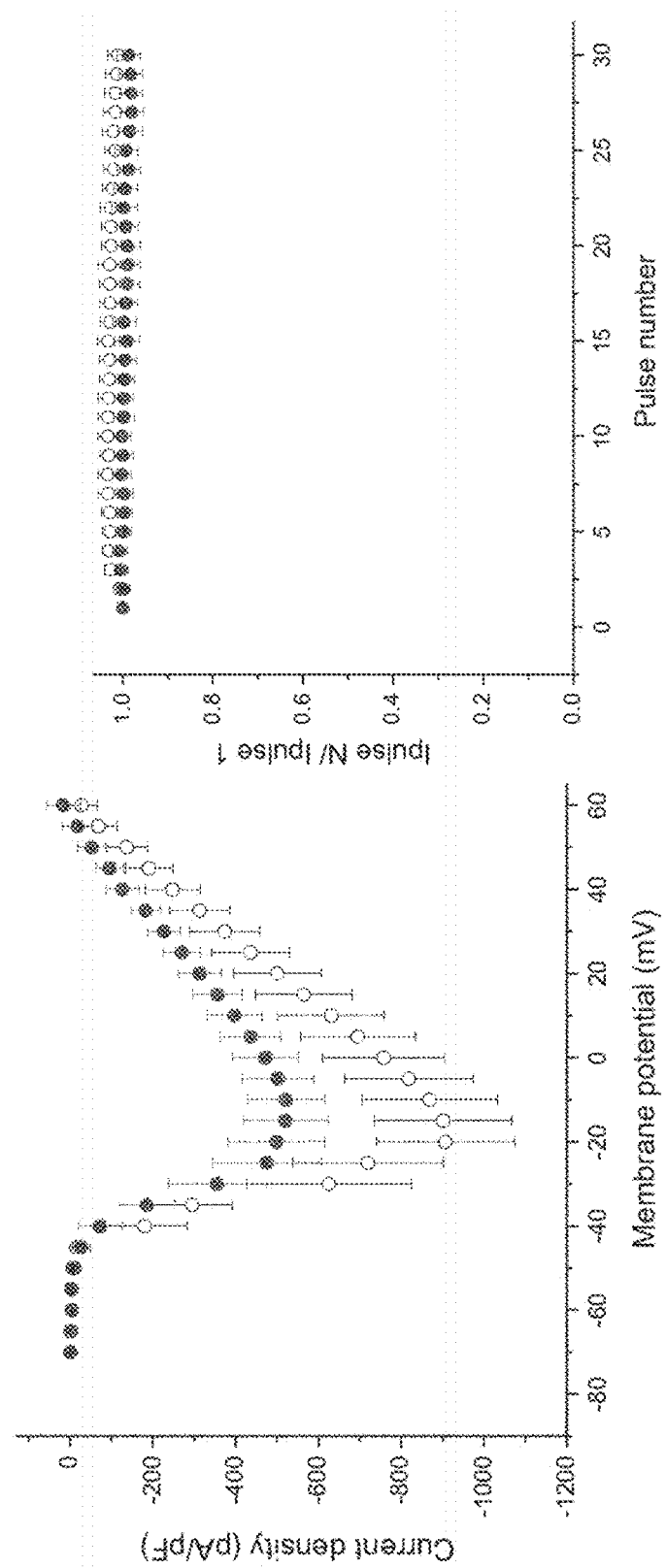

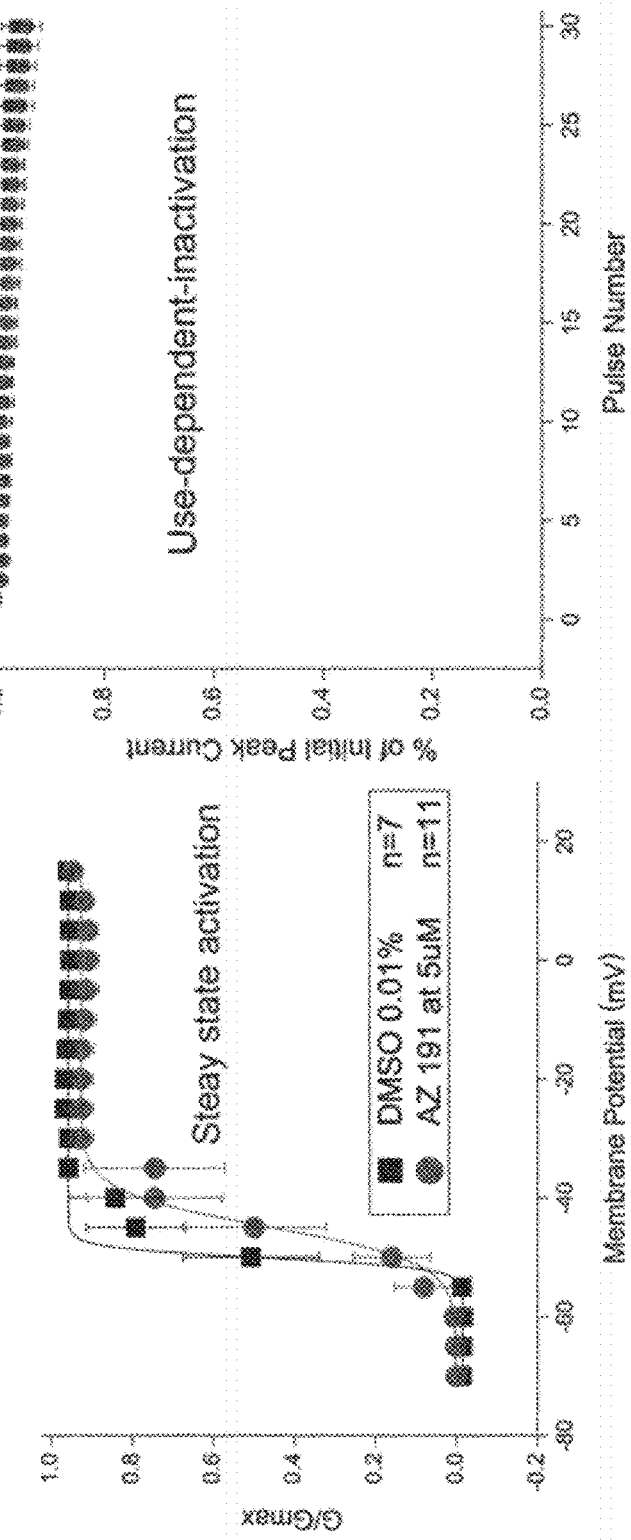

CRMP2 SUMOYLATION INHIBITORS AND USES THEREOF

CROSS-REFERENCE TO RELATED APPLICATIONS

This application is a continuation of U.S. patent application Ser. No. 15/766,299 filed Apr. 5, 2018, which is a Section 371 U.S. national stage entry of International Patent Application No. PCT/US2016/056051, International Filing Date Oct. 7, 2016 which claims the priority benefit of U.S. Provisional Application No. 62/238,182, filed Oct. 7, 2015, which is incorporated herein by reference in their entirety.

FIELD OF THE INVENTION

The present invention relates to compounds that can modulate the amount of voltage-gated sodium channel Nav1.7 protein that is present on neuronal surface and methods for using such compounds. In particular, it is believed that compounds of the invention modulate the amount of Nav1.7 protein on the cellular surface by inhibiting SUMOylation of CRMP2, where SUMOylation is the addition of small ubiquitin-like modifier (SUMO).

BACKGROUND OF THE INVENTION

Chronic pain, and in particular neuropathic pain, affects millions of individuals, costs billions of dollars, and is a major cause of morbidity, suffering, and suicide. Although some chronic pain conditions can be treated adequately with existing drugs, a large number of patients fail to achieve adequate pain relief, even with polypharmacy. Furthermore, currently available opioid pain therapies, which are generally only partially effective, are often associated with many side effects that limit their clinical efficacy, including tolerance and addiction.

Current understanding of neuropathic pain mechanisms at the molecular and cellular levels is incomplete. As such, conventionally prescribed analgesic medications are only successful in approximately a third of afflicted patients.

Therefore, new research and therapies are needed to further understand pain mechanisms that can open new avenues for specific and more effective treatments.

SUMMARY OF THE INVENTION

Some aspects of the invention are directed to SUMOylation inhibitors of CRMP2. It is believed that inhibiting SUMOylation of CRMP2 results in reduction in the number of Nav1.7 proteins on the cellular surface, thereby alleviating various clinical conditions associated with the excessive presence and/or hyper-activation of cellular surface Nav1.7. In some embodiments, SUMOylation inhibitors of CRMP2 is a compound is of the formula:

$$Ar^{a1}-L^{a1}-Ar^{a2}-Ra^{a1} \quad \text{(Compound I)};$$

where $Ar^{a1}$ is optionally substituted phenyl; $L^{a1}$ is a linker having a hydrogen bond acceptor moiety; $Ar^{a2}$ is phenylene, pyridylene or pyrazinylene, each of which is optionally substituted; $R^{a1}$ is heterocyclyl or heteroalkyl having at least one hydrogen bond acceptor; $Ar^{b1}$ is benzo[d][1,3]dioxolyl, benzo[d]oxazolyl, benzo[d]isoxazolyl, benzo[d]imidazolyl, naphthyl or quinolinyl; $L^{b1}$ is a conformationally constrained linker; $R^{b1}$ is heterocyclyl or nitrogen-heteroalkyl; $Ar^{c1}$ is 2,3-dihydrobenzo[b][1,4]dioxinyl, quinolonyl, benzoxazinyl, quinazolinyl or quinoxalinyl; $L^{c1}$ is a linker having a hydrogen bond acceptor moiety; and $R^{c1}$ is heterocyclyl or heteroalkyl having at least one hydrogen bond acceptor. One particular compound of Formula I is of the formula:

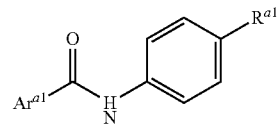

IA where $Ar^{a1}$ and $R^{a1}$ are those defined herein.

DETAILED DESCRIPTION OF THE INVENTION

Figure 1:
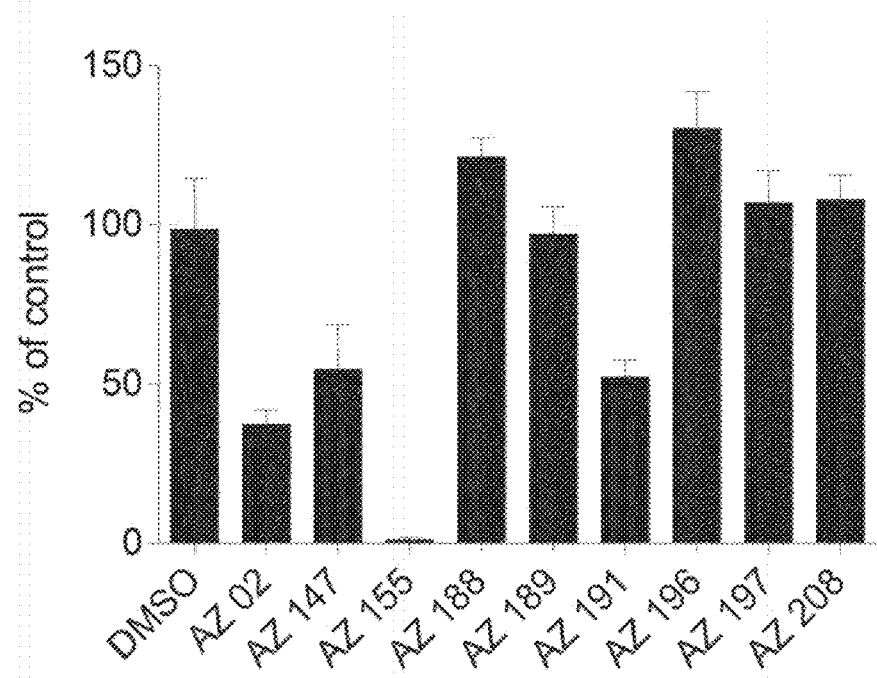
FIG. 1 is a bar graph showing ability of representative compounds of the invention to attenuate veratradine-induced increase in cytosolic Na in rat dorsal root ganglion (DRG) neurons in culture.
Figure 2A:
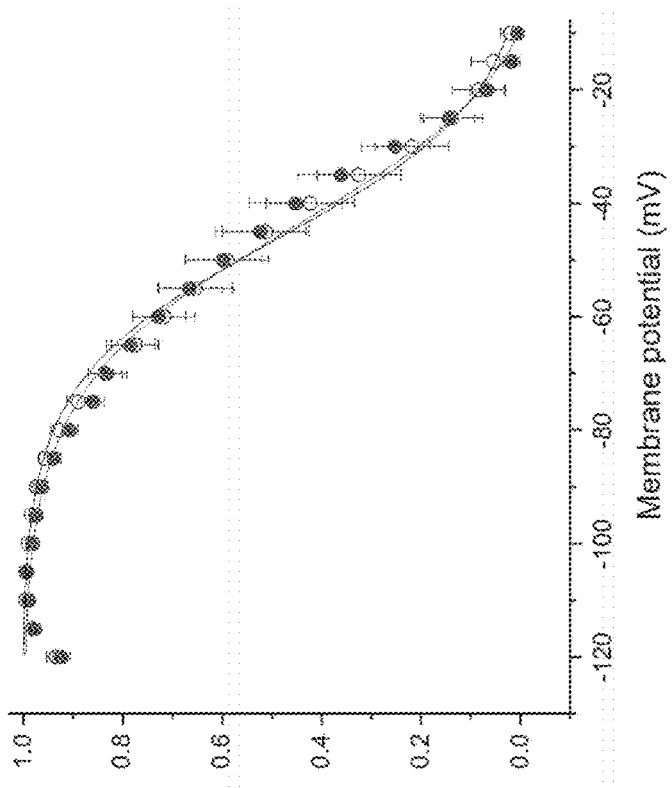
FIGS. 2A-4D show experimental results in graphic forms showing compounds of the invention inhibiting tetrodotoxin sensitive (TTX-S) NaV1.7 currents in rat DRGs. In each of these figures, panels A are graphic summary of activation, panels B are graphic summary of inactivation fits, panels C are graphs of current-voltage relationship, and panels D show use-dependent inactivation from rat DRGs treated with DMSO or the compounds of the invention.
Figure 2B:
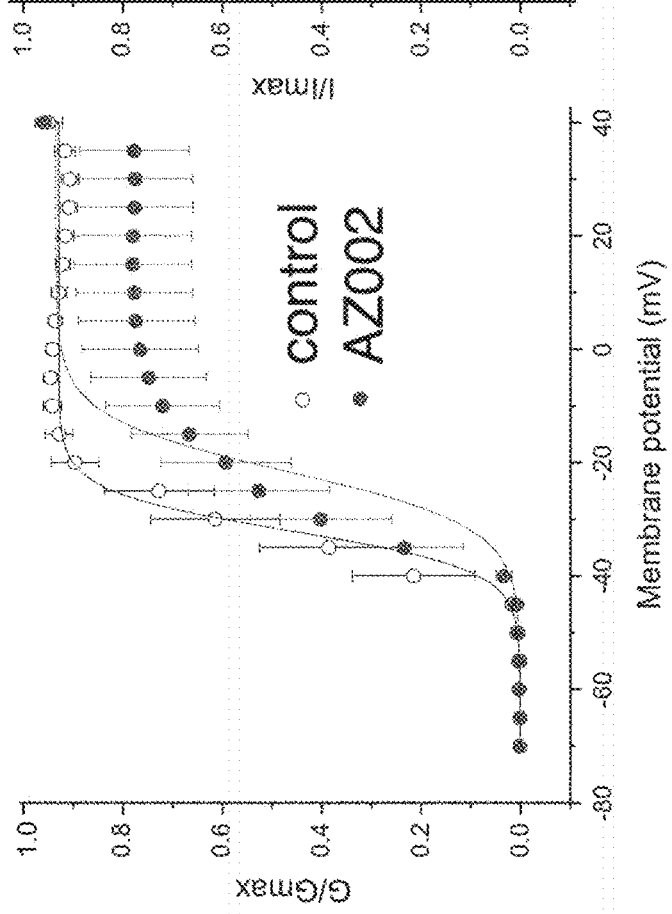
Figure 3A:
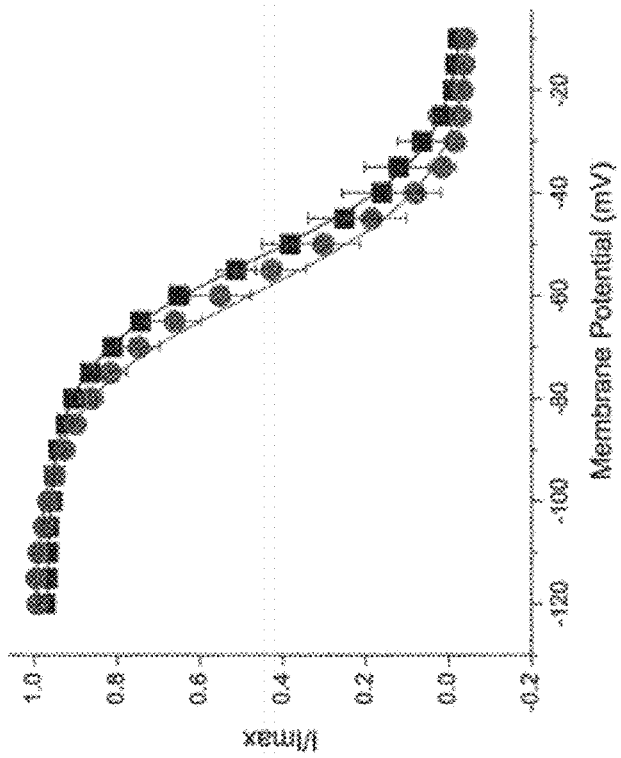
Figure 3B:
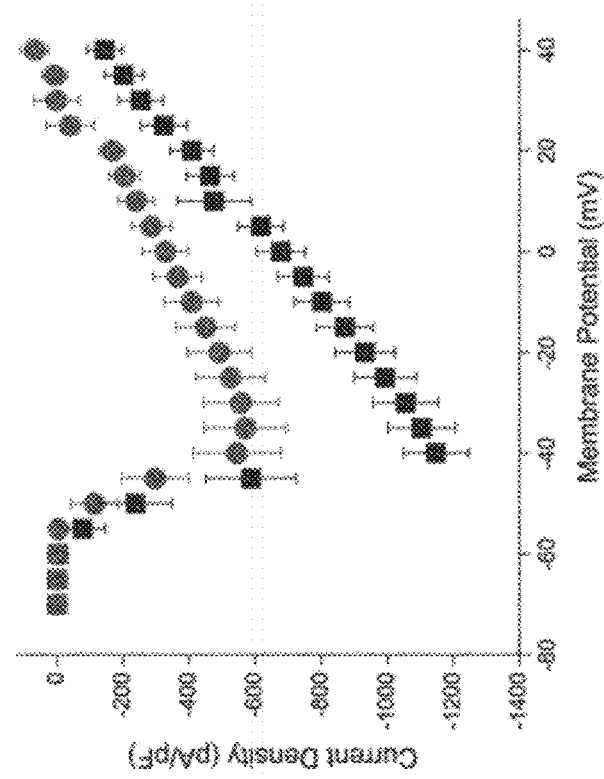
Figure 3D:
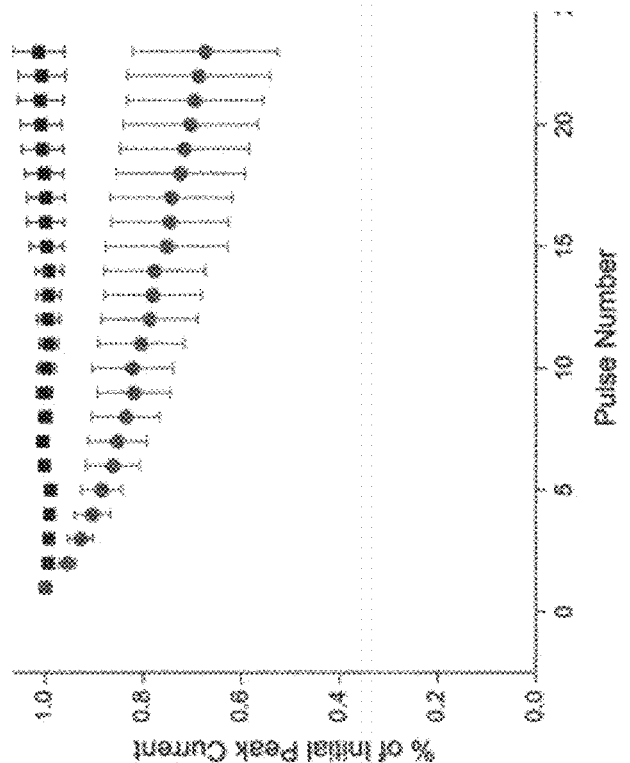
Figure 3C:
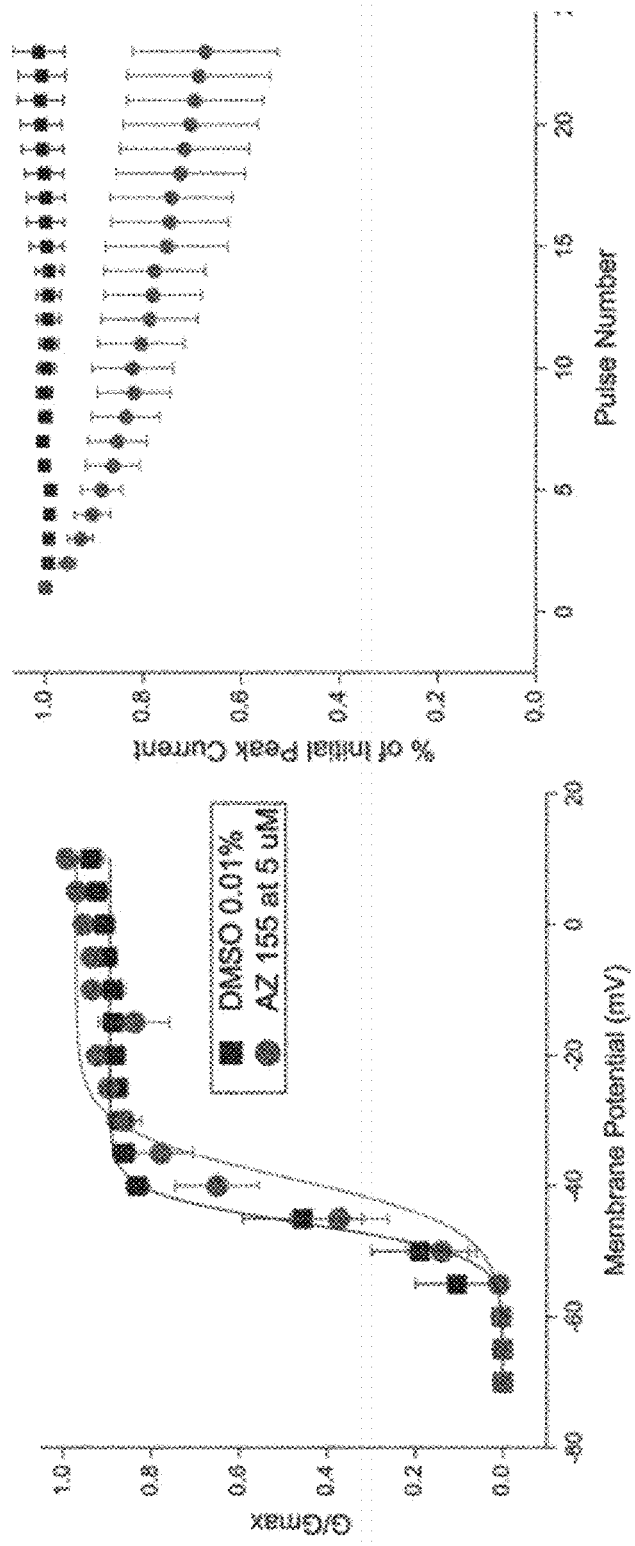

Definitions: Unless context requires otherwise, the following definitions are used throughout the specification. "Alkyl" refers to a saturated linear monovalent hydrocarbon moiety of one to twelve, typically one to six, carbon atoms or a saturated branched monovalent hydrocarbon moiety of three to twelve, preferably three to six, carbon atoms. Exemplary alkyl group include, but are not limited to, methyl, ethyl, n-propyl, 2-propyl, tert-butyl, pentyl, and the like. "Alkylene" refers to a saturated linear divalent hydrocarbon moiety of one to twelve, typically one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like. "Aryl" refers to a monovalent mono-, bi- or tricyclic aromatic hydrocarbon moiety of 6 to 15 ring atoms which is optionally substituted with one or more, preferably one, two, or three substituents within the ring structure. When two or more substituents are present in an aryl group, each substituent is independently selected. The terms "halo," "halogen" and "halide" are used interchangeably herein and refer to fluoro, chloro, bromo, or iodo. "Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like. "Heterocyclyl" means a non-aromatic monocyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclyl ring can be optionally substituted independently with one or more, preferably one, two, or three, substituents. When two or more substituents are present in a heterocyclyl group, each substituent is independently selected. "Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use. "Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like. "Protecting group" refers to a moiety, except alkyl groups, that when attached to a reactive group in a molecule masks, reduces or prevents that reactivity. Examples of protecting groups can be found in T.W. Greene and P.G.M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. "Corresponding protecting group" means an appropriate protecting group corresponding to the heteroatom (i.e., N, O, P or S) to which it is attached. "A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. As used herein, the terms "those defined above" and "those defined herein" when referring to a variable incorporates by reference the broad definition of the variable as well as any narrow and/or preferred, more preferred and most preferred definitions, if any.

Compounds of the Invention: Chronic pain is a major public health problem, affecting more than 100 million Americans. Opioids are powerful analgesics and the cornerstone of pain management for many types of pain. However, opioids can produce many side effects, including constipation, nausea, mental clouding, and respiratory depression, which can sometimes lead to death. Targeting voltage gated sodium channel Nav1.7, a protein linked to a broad range of pain conditions, has emerged as a strategy for development of pain therapeutics.

Some aspects of the invention are based on the discovery by the present inventors of compounds that can either directly or indirectly regulate the amount of Nav1.7 protein that is present on the cellular surface. Thus, compounds of the invention can be used to treat any number of clinical conditions that is associated with the presence of Nav1.7 on cellular surface. In one particular embodiment of the invention, compounds of the invention are used to treat pain including chronic and/or acute pain.

It is believed that the voltage-gated Nav1.7 sodium channel is preferentially expressed in the peripheral nervous system within ganglia related to nociceptive pain, including dorsal root ganglia (DRG), trigeminal ganglia and sympathetic ganglia. In nociceptive neurons responsible for the transduction of pain signals, the channel modulates voltage activation threshold required to fire action potentials in response to stimuli. Gain-of-function mutations, i.e., those that lower Nav1.7 current threshold for initiation of action potentials, produce allodynia—a lowered stimulus threshold for pain. Such mutations are the cause of pain syndromes including erythromelalgia, paroxysmal extreme pain disorder, and small fiber neuropathy.

Increased presence of Nav1.7 on cellular surface has also been associated with pain resulting from diabetic neuropathy, inflammation, following combined sciatic nerve compression, nucleus pulposus application modeling lumbar disc herniation, and after spared nerve injury (SNI). Conversely loss-of-function mutations in Nav1.7 prevent stimuli from reaching threshold to propagate pain. Patients with such mutations display a complete loss of pain sensation. In addition, herpes vector-mediated knockdown of Nav1.7 in DRG sensory neurons significantly prevents the development of hyperalgesia (i.e., an increased response to a painful stimulus) in response to complete Freund's adjuvant. Thus, Nav1.7 is both sufficient and necessary for pain transduction. In fact, as evidence of such a role, it has been shown that Nav1.7 knockout mice fail to develop hyperalgesia in inflammatory and neuropathic pain models, yet do not express phenotypic deficits.

Without being bound by any theory, it is believed that compounds of the invention modulate the amount of Nav1.7 protein that is present on cell surface and therefore the cellular excitability controlled by this protein. In particular, it is believed that compounds of the invention modulate (e.g., inhibit) an intracellular process that is responsible for effectuating the cellular trafficking of a particular voltage gated sodium channel to the cellular surface, thereby selectively reducing the presence of this channel (i.e., Nav1.7 protein) on the cell surface.

Without being bound by any theory, it is believed that compounds of the invention are believed to inhibit CRMP2 SUMOylation process. SUMOylation is a post-translational modification involved in various cellular processes. The term "SUMO" refers to Small Ubiquitin-like Modifier. SUMO proteins are a family of small proteins that covalently attach to and detach from target proteins in cells to modify their function. As used herein, modulating or inhibiting "SUMOylation" or "SUMOylation process" means modulating or inhibiting attachment of SUMO proteins and/or modulating or inhibiting modification of a protein after attachment of SUMO proteins.

The amount of Nav1.7 protein present on the cellular surface is modulated in part by SUMOylation of CRMP2 protein, i.e., CRMP2. CRMP2 is a member of the collapsin response mediator protein (CRMP) family that consists of five intracellular phosphoproteins (CRMP1, CRMP2, CRMP3, CRMP4, CRMP5) of similar molecular size (60-66 kDa). It has been found that compounds that can modulate expression or biological activity of CRMP2 also can be used to treat clinical conditions associated with neurological diseases such as Multiple Sclerosis, Alzheimer's disease, Parkinson's disease, and stroke. Accordingly, in some embodiments, compounds of the invention can be used to treat neurological diseases such as Alzheimer's disease, Parkinson's disease, and/or stroke including the pain associated with some of these diseases.

With regards to pain treatment, compounds of the invention can be used to treat various types of pain including chronic pain and acute pain, and itch as well as anosmia. Exemplary chronic pains that can be treated with compounds of the invention include, but are not limited to, cancer pain, burn pain, arthritic pain, chemotherapy-induced peripheral neuropathy, post-herpetic neuralgia, episodic pain such as primary erythromelalgia and paroxysmal extreme pain disorder, etc. Exemplary acute pains that can be treated by compounds of the invention include, but are not limited to, noxious heat pain, itch, and surgical pain.

Compared to traditional pain treatment using an opioid compound, some of the advantages of compounds of the invention include, but are not limited to, no motor impairment or sedation, higher potency and equivalent efficacy to morphine and gabapentin at a given dose level, and non-existent or vastly reduced potential for rewarding effect and potential for abuse compared to narcotic analgesics.

Other aspects of the invention include methods for treating pain in a subject, said method comprising administering to a subject in need of such treatment a therapeutically effective amount of a compound of the invention. Another aspect of the invention include a method for treating a clinical condition associated with the presence and/or activation of Nav1.7 protein on cellular surface, said method comprising administering a therapeutically effective amount of a compound of the invention to a subject suffering from a clinical condition associated with the presence and/or activation of Nav1.7 protein on the cellular surface thereby reducing the amount of Nav1.7 protein on the cellular surface. Without being bound by any theory, it is believed that compounds of the invention reduce the amount of Nav1.7 present on the neuronal cellular surface by inhibiting SUMOylation of CRMP2.

Some of the representative compounds of the invention include, but are not limited to, compounds of the formula:

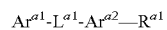 (Compound I);

$Ar^{a1}$-$L^{a1}$-$Ar^{a2}$—$R^{a1}$

In Compound of Formula I, $Ar^{a1}$ is optionally substituted aryl such as phenyl or pyridine. In one embodiment, $Ar^{a1}$ is substituted phenyl with a substituent on the 3-, 4- and/or the 5-position (relative to the carbon having $L^{a1}$, which is arbitrarily designated as the C1-position). Exemplary substituents for phenyl group (e.g., $Ar^{a1}$ and $Ar^{a2}$) in Compound of Formula I (or any other phenyl group in compounds of the invention) include alkoxy (e.g., methoxy, isopropyloxy, etc.), cycloalkoxy (e.g., cyclopropyloxy), aryloxy, (e.g., phenoxy, where phenyl group of phenoxy is optionally substituted as described herein), alkyl, haloalkyl, haloalkoxy (i.e., R—O—, where R is haloalkyl, such as trifluoromethoxy etc.), fluoro, cyano, aralkoxy (i.e., Ar—R—O—, where Ar is aryl and R is alkylene, such as benzyloxy, where the aryl group is optionally substituted with 1-3 substituents, such as those describe above), and heterocyclylalkoxy (i.e., Het-R—O—, where Het is heterocyclyl and R is alkylene). Typically, the 3- and/or 4-positions of phenyl $Ar^{a1}$ is substituted with a relatively hydrophobic ether group. The 5-position of phenyl $Ar^{a1}$ is typically substituted with a H-bond acceptor. The terms "H-bond acceptor" and "H-bond acceptor moiety" are used interchangeably herein and refer to a heteroatom (e.g., O, N, S, P, etc.) that has a lone-pair of electrons that can form a hydrogen bond with a molecule having a hydrogen atom that is bound to a highly electronegative atom such as nitrogen (N), oxygen (O) or sulfur (S), etc. See, for example, en.wikipedia.org/wiki/Hydrogen_bond. Exemplary H-bond acceptors that are suitable in $Ar^{a1}$ include, but are not limited to, oxygen containing substituents such as alkoxy and haloalkoxy (e.g., methoxy, ethoxy, propoxy, isopropoxy, and trifluoromethoxy).

$L^{a1}$ of Compound of Formula I is a linker having a hydrogen bond acceptor moiety. In one particular embodiment, $L^{a1}$ is a moiety of the formula: —C(=O)—NR—, where R is hydrogen, alkyl or a nitrogen protecting group. In another embodiment, $L^{a1}$ is imidazolyl moiety (e.g., with two N-atoms of imidazolyl in 1,3-postion of the ring).

$Ar^{a2}$ is of Compound of Formula I is phenylene, pyridylene or pyrazinylene, each of which is optionally substituted with 1-3 substituents, each of which is independently selected. Suitable substituents include those described above. It should be appreciated that all $Ar^{a2}$ is substituted with $R^{a1}$, thus when referring to $Ar^{a2}$ as being substituted, it is meant that $Ar^{a2}$ has at least one other substituent besides $R^{a1}$. Typically $R^{a1}$ is substituted on the para-position relative to $L^{a1}$ group. Particularly, suitable substituents for $Ar^{a2}$ include halo (e.g., chloro, bromo, iodo and/or fluoro), alkyl, alkoxy, haloalkyl, alkylamino, alkyloxyalkylamino, etc.

$R^{a1}$ of Compound of Formula I is heterocyclyl or heteroalkyl having at least one hydrogen bond acceptor. Exemplary heterocyclyls that are suitable for $R^{a1}$ include, but are not limited to, piperazin-1-yl (e.g., 4-methyl or 4-alkyl piperazin-1-yl), morpholinyl, pyrrolidinyl, piperidinyl, etc. Alternatively, $R^{a1}$ can be a moiety of the formula: —NH—$(CH_2)_m$—$OR_3$ or a moiety of the formula: —NH—$(CH_2)_m$—$N(R_4)(R_5)$, where, m=is an integer 2 or 3, $R_3$ is hydrogen, alkyl or a hydroxyl protecting group, and $R_4$ and $R_5$ are independently selected from the group consisting of hydrogen, alkyl, cycloalkyl or $R_4$ and $R_5$ together with the nitrogen atom to which they are attached to form a substituted or unsubstituted ring system with optionally one or more additional heteroatoms within the ring system.

In other embodiments, $R^{a1}$ is heteroalkyl. Typically, heteroalkyl of $R^{a1}$ include a H-bond acceptor such as a basic amine group, carbonyl (i.e., —C(=O)—) group, alkoxy, aryloxy or a combination thereof.

In one embodiment, Compound I is of the formula:

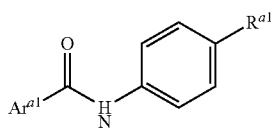

IA where $Ar^{a1}$ and $R^{a1}$ are those defined herein. Specific examples of $Ar^{a1}$ include, but are not limited to, 3,5-dimethoxyphenyl; 3-methoxyphenyl; 3-isopropoxyphenyl; 3,4,5-trimethoxyphenyl; 3-fluoro-4[2-(piperidin-1-yl) ethoxy]phenyl or a salt thereof 3-methoxy-4-[(4-trifluoromethoxyphenyl)methoxy]phenyl; benzo[d][1,3]dioxol-5-yl; 3-fluoro-4-[2-(morpholino)ethoxy]phenyl; 3-methoxy-4-[(3-fluorophenyl)methoxy]phenyl; 3-methoxy-4-[(4-fluorophenyl)methoxy]phenyl; 3-methoxy-4-[(3-trifluoromethylphenyl)methoxy]phenyl; 3-methoxy-4-[(4-cyanophenyl)methoxy]phenyl; and the like. Specific example of $R^{a1}$ include, but are not limited to, 4-methylpiperazinyl and a salt thereof 4-acetylpiperazinyl; 4-methoxypiperadinyl; and other substituted piperazinyl and piperadinyl moieties.

In general, any compound that can modulate (e.g., interfere or inhibit) SUMOylation of CRMP2 is within the scope of the invention. Such a compound can be readily identified by using in silico or in vitro assay methods disclosed in the Examples section. To develop a CRMP2 SUMOylation inhibitor that can be used to control the number (i.e. amount) of Nav1.7 on the neuronal cellular surface, a high-throughput assay was used to test the ability of Ubc9, an E2 SUMO conjugating enzyme, to bind to CRMP2. Briefly, purified CRMP2-His protein bound to a Ni-chelate acceptor bead was incubated with Ubc9-GST protein bound to a glutathione coated donor bead. When an acceptor bead came into proximity with a donor bead, the acceptor bead emitted a fluorescence signal between 520-620 nm. The donor bead contained a photosensitizer, phthalocyanine that converts ambient oxygen to an excited singlet form of oxygen. This singlet oxygen reacts with a thioxene derivative on the acceptor bead culminating in a chemiluminescent reaction. This reaction occurs only if the beads are within about 200 nanometers of each other. The strength of the singlet oxygen reaction is also proportional to the amount of analyte present, and thus can be used for screening. Using this bead-based Amplified Luminescent Proximity Homogeneous Assay (ALPHA) technology (Perkin Elmer), the putative interaction between CRMP2-His and Ubc9-GST was examined. It was discovered that Ubc9 bound with sub-micromolar affinity to CRMP2; this binding was stable over at least an 18 hour period.

Some of the methods that can be used to produce compounds of the invention are illustrated below:

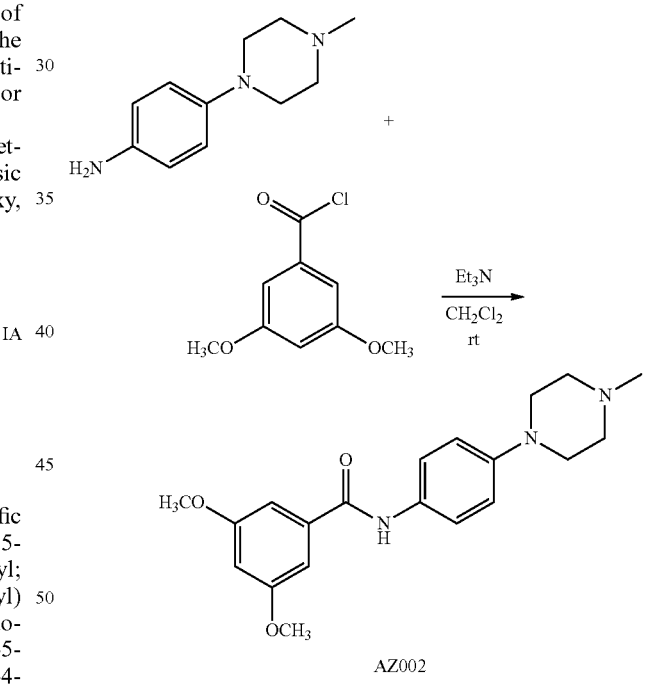

As can be seen above, typically an appropriate aromatic compound (i.e., left-portion of the compounds) is used as a starting material and the desired moieties are attached and transformed to a desired right-portion of the compound. By using different "left-portion" as well as a different "right-portion," a wide variety of compounds of the invention can be prepared. Further transformation of the substituents either in the intermediate and/or the product can also be performed to produce compounds having different substituents. Specific examples of compounds of the invention include, but are not limited to, the following compounds:

AZ002
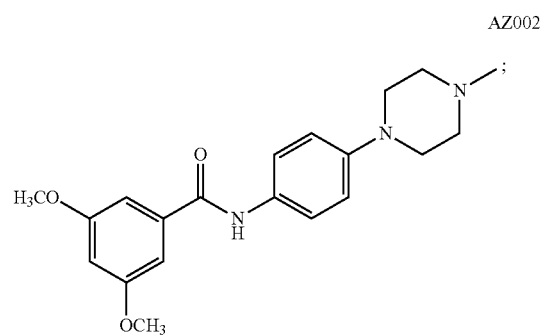
AZ155
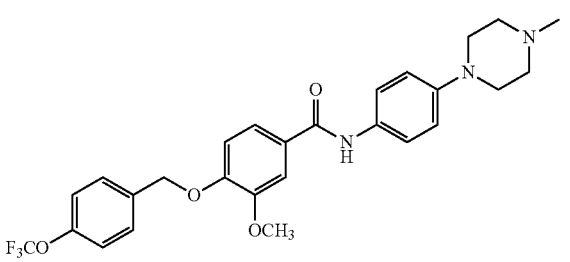
AZ038
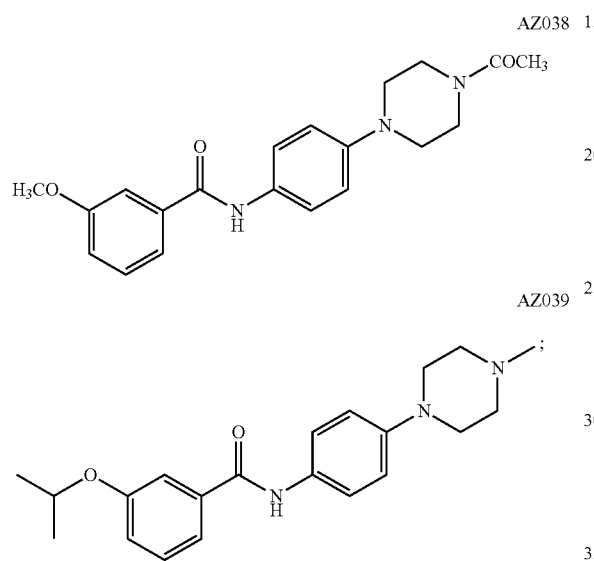
AZ188
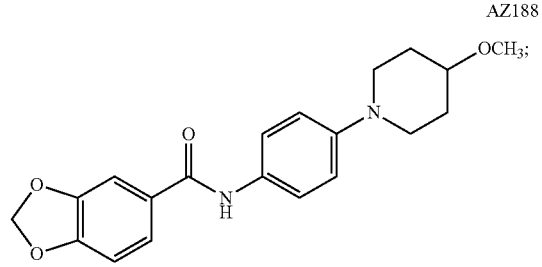
AZ039
AZ189
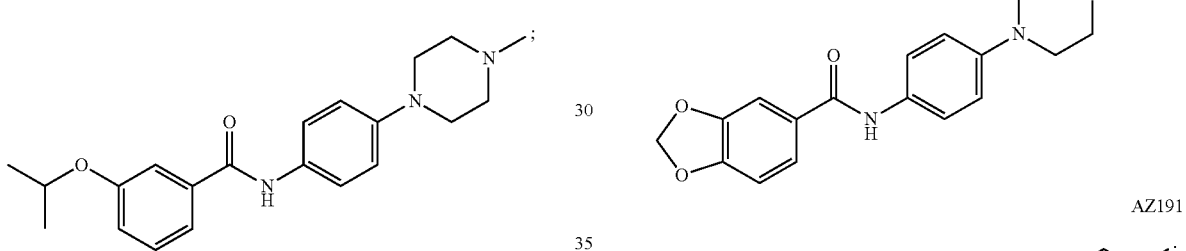
AZ040
AZ191
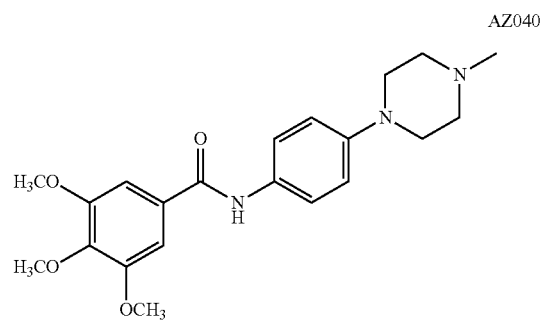
AZ196
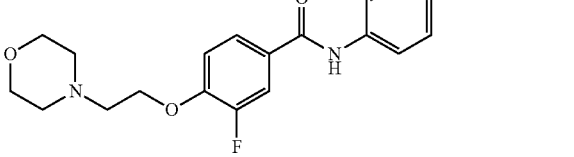
AZ147
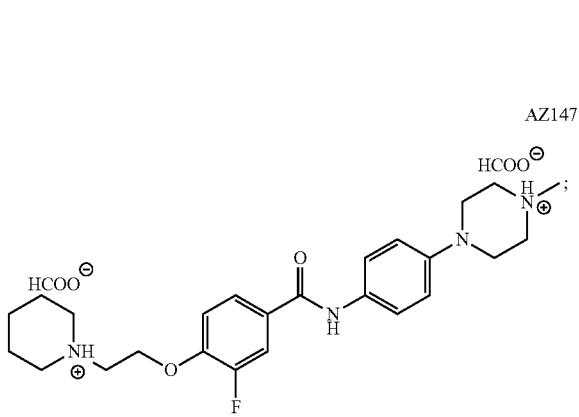
AZ197
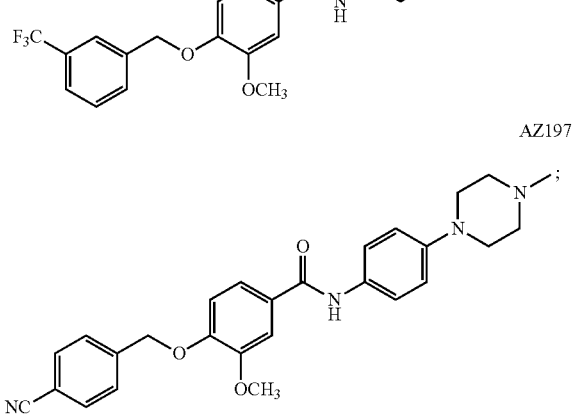

-continued

AZ208

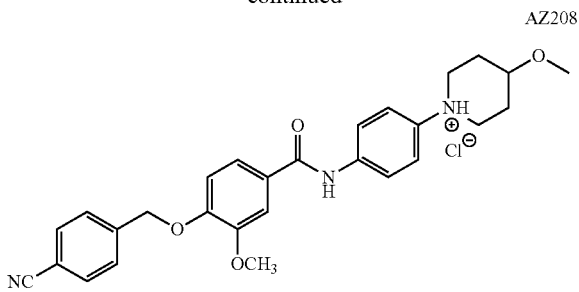

Some PK profiles of compound AZ002 are: $t_{max}$=2 hr, $C_{max}$=263.1 ng/ml, AUC (0-24 hr)=2375.1 hr·ng/ml, $t_{1/2}$=5.8 hr, and bioavailability (F)=31%. In some instances, compounds of the invention are provided as a pharmaceutical acceptable salt. Suitable pharmaceutical acceptable salts include those disclosed herein. In some embodiments, pharmaceutically acceptable salts of compounds of the invention provide a better pharmacokinetics. For example, pharmacokinetics ("PK") analysis of compound AZ002 hydrochloride salt showed greater solubility than compound AZ002 itself, inhibited NaV1.7 currents by ~45% without affecting other CRMP2-mediated functions.

Biological data of some of the compounds showing effectiveness are shown in FIGS. 1-5. Briefly, FIG. 1 is a data showing ability of representative compounds of the invention to attenuate veratradine-induced increase in cytosolic $Na^+$ in rat dorsal root ganglion (DRG) neurons in culture. This is indicative of compounds ability to reduce sodium influx via voltage-gated Nav.17 channels that are linked to pain. DRG neurons were loaded with Fura2-AM, a $Ca^{2+}$-sensitive dye and then were treated with 30 μM veratradine to open $Na^+$ channels alone (DMSO) or with 5 μM AZ compounds. The veratradine-induced changes in intracellular sodium concentration ($[Na^+]c$) over time were quantified by calculating the area under the curve (AUC) for 120 seconds following application of veratradine and the AZ compounds. Data shown are mean±SEM. N=4 independent experiments (n=104-520 cells per experiment).

Figures 4A, 4B:
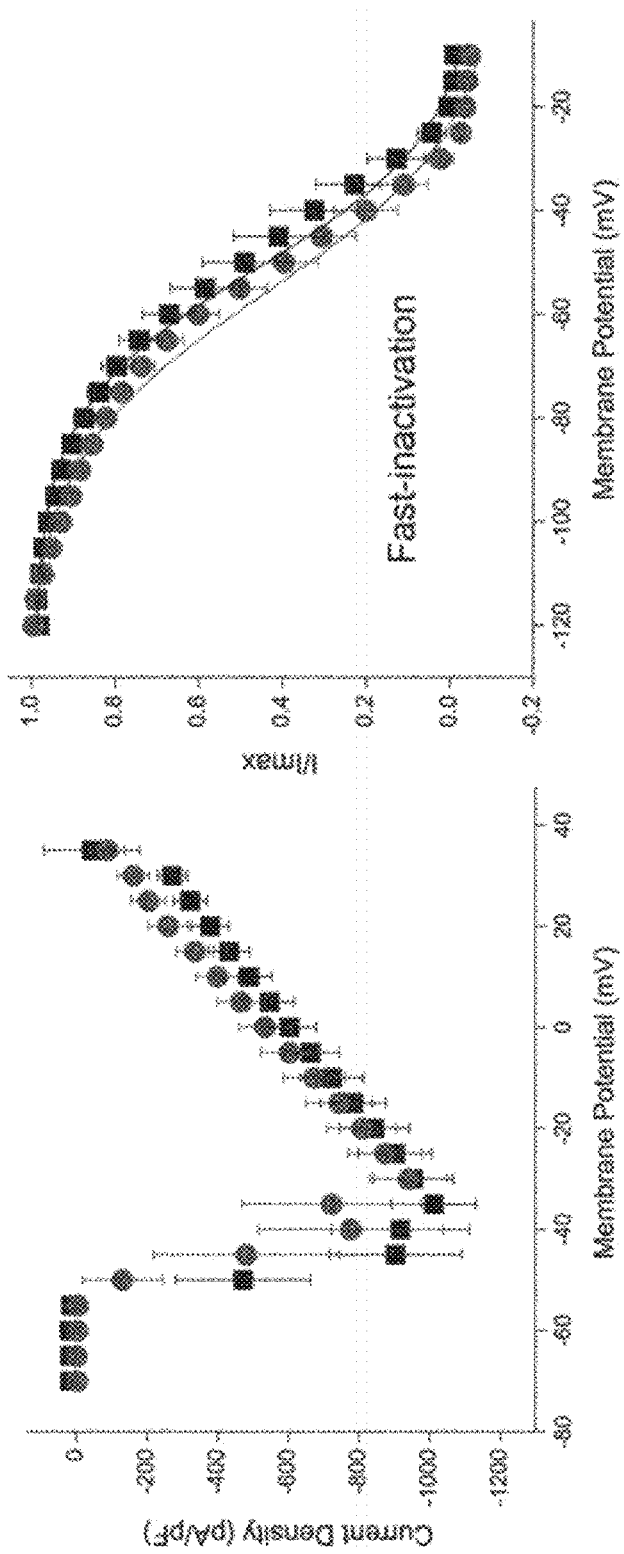

FIGS. 2A-4D show effects of compounds AZ002, AZ155 and AZ191 on tetrodotoxin sensitive (TTX-S) NaV1.7 currents in primary rat DRGs. Summary of activation are showing in FIGS. 2A, 3A and 4A, respectively. Summary of inactivation fits are shown in FIGS. 2B, 3B and 4B, respectively. FIGS. 2C, 3C and 4C show current-voltage relationship of compounds AZ002, AZ155 and AZ191, respectively. FIGS. 2D, 3D and 4D show use-dependent inactivation from rat DRGs treated with DMSO or compound Az002, AZ155 or AZ191, respectively. Data are mean±SEM. N=10 to 11 cells as indicated.

Figure 5:
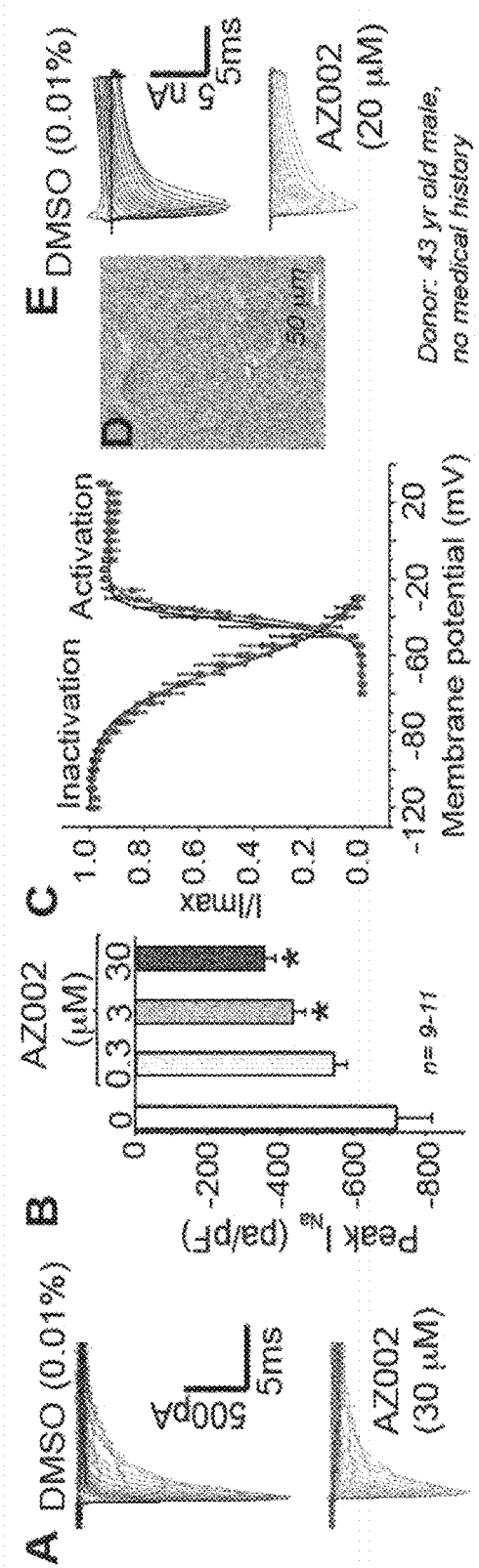
FIG. 5 is experimental results of a compound of the invention inhibiting TTX-S NaV1.7 currents in rat and human DRGs. Panel A shows representative family of sodium current traces. Panel B shows summary peak currents of compound AZ002. Panel C shows activation and inactivation fits from rat DRGs treated with DMSO or a compound of the invention. Panel D is a photograph showing two human DRGs (yellow arrows) in a mixed glia-DRG co-culture demonstrating that overnight incubation with AZ002 does not affect cell morphology or health. Panel E shows family of current traces demonstrating inhibition of H-infinity subtracted (i.e., NaV1.7) currents in human DRGs treated with AZ002.

FIG. 5 shows compound AZ002 inhibits TTX-S NaV1.7 currents in rat and human DRGs. Panel A shows sodium current traces of control (DMSO) and compound AZ002 treated DRGs. Panel B shows summary peak currents of DRGs treated with various concentrations of AZ002. Panel C is a graph of activation and inactivation fits. Panel D is a photograph of human DRGs (yellow arrows) in a mixed glia-DRG co-culture. Panel E is family of traces showing H-infinity subtracted (i.e. NaV1.7) currents from control (DMSO treated) or AZ002 compound treated human DRGs. *, P<0.05 (Student's t-test).

Pharmaceutical Composition: The present invention includes pharmaceutical compositions comprising at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intra-arterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula (I), as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula (I) or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula (I), or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

In Silico Modeling: In silico docking of compounds to human CRMP2 was performed. Briefly, the structure of human CRMP2 with 53 docked compounds was analyzed. Computational screening was used to search for small molecules that bind to CRMP2. Docking was focused on a 10 Å$^3$ pocket on CRMP2 that accommodates the K374 residue within the SUMOylation motif. The resulting complexes were ranked using Glide score and other energy related terms. Most compounds docked onto 2 distinct sites on CRMP2. Glide scores from docking of compounds onto the crystal structures of CRMPs 1, 4, and 5 were used to identify lead compounds.

Screening Assay: Screening for Ubc9-CRMP2 inhibitors by ALPHA assay was performed. Briefly, 100 µM of compounds identified as lead compounds in in silico modeling were assayed for percent inhibition of the Ubc9-CRMP2 protein interaction to further identify lead compounds.

Veratradine induced screen: Veratridine, an inhibitor of NaV inactivation, increases the opening of Na$^+$ channels leading to a depolarization that results in opening of voltage-gated calcium channels. Calcium entry was monitored by a ratiometric Fura2-AM assay. Here, sensory neurons were incubated overnight with various compounds of the invention and tested for their ability to affect veratradine-induced calcium influx. Bars summarizing mean 340 nm/380 nm ratios in control (DMSO, 0.03%) and compounds were plotted. Data from >100 cells per condition were obtained. Compounds showing above-threshold value were deemed likely represent activators while those below the threshold value were identified as potential inhibitors of SUMOylation of CRMP2 that affect Nav1.7.

Rat Behavioral Pain Assay: Compound AZ002 reversed mechanical hypersensitivity in a model of nerve-injury induced chronic pain. The spinal administration of AZ002 (5 µg/10 µL) significantly reversed mechanical hypersensitivity in spared nerve injury model of neuropathic pain. Paw withdrawal threshold resulted in a significant decrease 7 days post-injury that was significantly reversed at times 30 to 240 minutes following AZ002 administration (n=6, *p<0.05) but not vehicle control (DMSO).

In addition, the spinal administration of AZ002 (5 µg/10 µL) and AZ008 (5 µg/10 µL) significantly reversed mechanical hypersensitivity in spared nerve injury model of neuropathic pain. Paw withdrawal threshold resulted in a significant decrease 7 days post-injury that was significantly reversed at times 15, 30, 90 and 120 minutes following AZ002 administration (n=6, *p<0.05) and at times 90, 120, 150 and 210 minutes following AZ008 administration (n=6, *p<0.05). Data was analyzed using one-way ANOVA followed by Dunnett's Multiple Comparison Test using post injury baseline as control.

Culturing and transfection of catecholamine A differentiated (CAD) and human embryonic kidney 293 (HEK293) cell lines: Mouse neuron derived CAD and human derived HEK293 cells were grown in standard cell culture conditions, 37° C. in 5% $CO_2$. All media was supplemented with 10% FBS (Hyclone) and 1% penicillin/streptomycin sulfate from 10,000 µg/ml stock. CAD cells were maintained in DMEM/F12 media and HEK293 cells were maintained in DMEM media. HEK293 cell lines expressing various NaV1.X isoforms were obtained from Dr. Theodore R. Cummins (Indiana University School of Medicine). HEK293 cells stably expressing NaV1.X subtypes were generated by calcium phosphate precipitation transfection of hNaV1.1 in pTarget vector, rNaV1.3 or hNaV1.7 in pcDNA3.1-mod vector, or hNaV1.5 in pRcCMVII vector. Geneticin (Cat #10131035, Thermo Fisher Scientific, Waltham, Mass.) was used at 500 µg/ml to select for NaV1.X expressing cells. CAD cells were chosen as a model neuron cell line due to ~80% contribution by NaV1.7 to total sodium currents. This ~80% contribution was determined by isoform-specific blockade of NaV1.7 by both HWTX-IV (Alomone Laboratories, Jerusalem, Israel) and ProTox-II (Sigma, St. Louis, Mo.). Cells were transfected using 1 µg/µl polyethylenimine (PEI) (Sigma, St. Louis, Mo.) complexed with 2 µg/µl CRMP2 plasmid and/or 1 µg/µl other indicated plasmids. Under these conditions, transfection efficiencies were ~50%. In order to attain higher transfection efficiency required for protein quantification, several Western blots were performed on cells transfected with Lipofectamine 2000 (Cat #11668019, Thermo Fisher Scientific, Waltham, Mass.) according to manufacturer's instructions. In these cases transfection efficiency was typically >95%. siRNAs were transfected using Lipofectamine 2000 according to manufacturer's instructions at a concentration of 500 nM. All experiments were performed between 48 h and 72 h after transfection. Plasmid transfection was verified by dsRed fluorescence and knockdown was verified by Western blot.

Culturing and Transfection of rat Primary Dorsal Root Ganglia (DRG) Neurons: Rat DRG neurons were isolated from 150-174 g Sprague-Dawley rats and then transfected using known procedures. In brief, removing dorsal skin and muscle and cutting the vertebral bone processes parallel to the dissection stage exposed DRGs. DRGs were then collected, trimmed at their roots, and digested in 3 ml bicarbonate free, serum free, sterile DMEM (Cat #11965, Thermo Fisher Scientific, Waltham, Mass.) solution containing neutral protease (3.125 mg·ml-1, Cat #LS02104, Worthington, Lakewood, N.J.) and collagenase Type I (5 mg·ml-1, Cat #LS004194, Worthington, Lakewood, N.J.) and incubated for 45 min at 37° C. under gentile agitation. Dissociated DRG neurons (~1.5×106) were then gently centrifuged to collect cells and washed with DRG media DMEM containing 1% penicillin/streptomycin sulfate from 10 000 μg/ml stock, 30 ng.ml-1 nerve growth factor, and 10% fetal bovine serum (Hyclone). Collected cells were re-suspended in Nucleofector transfection reagent containing plasmids or siRNA at the working concentrations listed above. Then, cells were subjected to electroporation protocol O-003 in an Amaxa Biosystem (Lonza, Basel, Switzerland) and plated onto poly-D-lysine—and laminin-coated glass 12- or 15-mm coverslips. Transfection efficiencies were routinely between 20% and 30% with about ~10% cell death. Small diameter neurons were selected to target Aδ- and c-fiber nociceptive neurons. For rat DRG culture small cells were considered to be ~<30 μm.

Patch Clamp Electrophysiology: Whole cell voltage clamp and current clamp recordings were performed at room temperature using an EPC 10 Amplifier-HEKA. The internal solution for voltage clamp CAD cell recordings contained (in mM): 110CsCl, 5 $MgSO_4$, 10 EGTA, 4 ATP Na2-ATP, and 25 HEPES (pH 7.3, 290-310 mOsm/L) and external solution contained (in mM): 100 NaCl, 10 tetraethylammonium chloride, 1 $CaCl_2$, 1 $CdCl_2$, 1 $MgCl_2$, 10 D-glucose, 4 4-aminopyridine, 0.1 $NiCl_2$, 10 HEPES (pH 7.3, 310-315 mosM/L). For DRG and HEK293 cells the internal solution for voltage clamp contained (in mM): 140CsF, 1.1Cs-EGTA, 10 NaCl, and 15 HEPES (pH 7.3, 290-310 mOsm/L) and external solution contained (in mM): 140 NaCl, 3 KCl, 30 tetraethylammonium chloride, 1 $CaCl_2$, 0.5 $CdCl_2$, 1 $MgCl_2$, 10 D-glucose, 10 HEPES (pH 7.3, 310-315 mosM/L). For DRGs the internal solution for current clamp contained (in mM): 140 KCl, 10 NaCl, 1 $MgCl_2$, 1 EGTA, 10 HEPES (pH 7.2), and 1 ATP-Mg (pH 7.3, 285-295 mOsm/L) and external solution contained (in mM): 154 NaCl, 5.6 KCl, 2 $CaCl_2$, 2.0 $MgCl_2$, 1.0 Glucose, and 10 HEPES (pH 7.4, 305-315 mOsm/L). In experiments where clathrin-mediated endocytosis was prevented with 20 μM Pitstop2 (Cat #ab120687, Abcam, Cambridge, Mass.), the compound was incubated in the tissue culture well for 30 m prior to the experiment. Electrodes were pulled from standard wall borosilicate glass capillaries from Warner Instruments with a P-97 electrode puller from Sutter Instruments and heat polished to final resistances of 1.5-3 megaOhms when filled with internal solutions. Whole-cell capacitance and series resistance were compensated with linear leak currents were digitally subtracted by P/4 method for voltage clamp experiments and bridge balance compensated in current clamp experiments. Signals were filtered at 10 kHz and digitized at 10-20 kHz. Cells wherein series resistance or bridge balance was over 15 megaOhm or fluctuated by more than 30% over the course of an experiment were omitted from datasets. Analysis was performed using Fitmaster software from HEKA and Origin9.0 software from OriginLab Corp.

Voltage clamp protocols: CAD and HEK293 cells were subjected to current-density (I-V) and fast-inactivation voltage protocols. In the I-V protocol, cells were held at a −80 mV holding potential prior to depolarization by 20 ms voltage steps from −70 mV to +60 mV in 5 mV increments. This allowed for collection of current density data to analyze activation of sodium channels as a function of current versus voltage and also peak current density which was typically observed near ~0-10 mV and normalized to cell capacitance (pF). In the fast-inactivation protocol, cells were held at a −80 mV holding potential prior to hyperpolarizing and repolarizing pulses for 500 ms between −120 mV to −10 mV in 5 mV increments. This step conditioned various percentages of channels into fast-inactivated states so that a 0 mV test pulse for 20 ms could reveal relative fast inactivation normalized to maximum current. DRGs from both rat and human were subjected to current-density (I-V) protocol and H-infinity (pre-pulse inactivation protocol). To estimate TTX-R contributions, I-V protocol was run after incubation with 500 nM TTX. Following holding at −100 mV, 200 ms voltage steps from −70 mV to +60 mV in 5 mV increments allowed for analysis of peak currents. The TTX-R peak current density was always measured at depolarizations near 0 mV and within 10 ms of the voltage step protocol. Given the previously identified properties of NaV1.8 and NaV1.9 TTX-R currents, this voltage-dependence and activation profile indicated analysis of peak current density of about NaV1.8 current. Thus, sodium current present at 150 ms following a voltage pulse to −60 mV was analyzed, an established method of isolating Nav1.9 current. In cells electroporated with CRMP2 plasmids, however, no Nav1.9 current was observed with this protocol. It is possible that analysis of NaV1.9 currents in response to changes of CRMP2 modification may require optimization of both recording solutions and transfection protocols. No inference should be made from this TTX-R current density data.

In the H-infinity protocol, cells were held at −100 mV and subjected to conditioning voltage steps for 1 s varying from −120 mV to 0 mV in 10 mV increments. This conditioning step was followed by a 0 mV test pulse for 200 ms to analyze current. The H-infinity protocol allowed subtraction of electrically isolated TTX-R (current available after −40 mV prepulse) from total current (current available after −120 mV prepulse) to estimate TTX-S current. This protocol is possible due to differential inactivation kinetics of TTX-R versus TTX-S channels wherein TTX-S current becomes activated and then fast-inactivated during the is −40 mV pulse. For all protocols, a test pulse was performed before and after the voltage protocol to evaluate run-down or run-up of currents during the voltage protocols and to omit data from cells with currents that were altered as a function of time.

Indwelling intrathecal catheter: Rats were anesthetized (ketamine/xylazine anesthesia, 80/12 mg/kg i.p.; Sigma-Aldrich) and placed in a stereotaxic head holder. The cisterna magna was exposed and incised, and an 8-cm catheter (PE-10; Stoelting) was implanted terminating in the lumbar region of the spinal cord. Catheters were sutured (3-0 silk suture) into the deep muscle and externalized at the back of the neck; skin was closed with autoclips. After a recovery period of 5-7 days after implantation of the indwelling cannula, the spared nerve injury was induced.

Spared Nerve Injury (SNI): Under isoflurane anesthesia (5% induction, 2.0% maintenance in 2 L/min air), skin on the lateral surface of the left hind thigh was incised. The biceps femoris muscle was bluntly dissected to expose the three terminal branches of the sciatic nerve. Briefly, the common peroneal and tibial branches were tightly ligated with 4-0 silk and axotomized 2.0 mm distal to the ligation. Sham animals underwent the same operation; however the exposed nerves were not ligated. Closure of the incision was made in two layers. The muscle was sutured once with 5-0 absorbable suture; skin was auto-clipped. Animals were allowed to recover for 5-7 days before any testing.

Mechanical Allodynia: Rats were allowed to acclimate within suspended wire mesh cages for 30 minutes prior to behavioral assessment. Before (pre-baseline), after SNI (post-baseline) and upto 5 hr were used to measure response to calibrated von Frey filaments (g) probed perpendicular to the lateral plantar surface of the left hind paw (up-down method). Paw withdrawal thresholds were calculated in grams using the Dixon non-parametric test and expressed as the Paw Withdrawal Threshold (mean±standard error; SEM) in GraphPad Prism 6.0. All behavior experiments were blinded.

Synthesis of Compounds: The following abbreviations are used: 1-Hydroxybenzotriazole (HOBt); Dichloromethane (DCM); Ethyl acetate (EtOAc); Methanol (MeOH); 2-(1H-benzotriazol-1-yl)-1,1,3,3-tetramethyluronium hexafluorophosphate (HBTU); N,N-diisopropylethylamine (DIPEA); N,N-dimethylformamide (DMF); Ethanol (EtOH); Triethylamine (Et$_3$N); Thin layer chromatography (TLC); Nuclear magnetic resonance (NMR); 1-Ethyl-3-(3-dimethylaminopropyl)carbodiimide (EDC) and 1-[Bis(dimethylamino)methylene]-1H-1,2,3-triazolo[4,5-b]pyridinium 3-oxid hexafluorophosphate (HATU).

General Procedure: All the chemicals were purchased from commercial vendors. All the solvents were obtained from Fischer Scientific. Flash chromatography was performed with silica gel (230/400 mesh, Fisher Scientific). All anhydrous reactions were carried out under positive pressure of nitrogen. HPLC-MS analyses were performed on an Agilent 1100 series instrument with a Zorbax C18 reverse-phase column. HRMS results were obtained on an apex-Qe instrument. All 1H-NMR and 13C-NMR spectra were recorded on a BRUKER AVANCE-III 400 MHz NMR instrument, using deuterated solvents. The spectra are reported in ppm and referenced to deuterated DMSO (2.49 ppm for 1H, 39.5 ppm for 13C) or deuterated chloroform (7.26 ppm for 1H, 77 ppm for 13C). High-resolution mass spectra (HRMS) were acquired on a Bruker 9.4 T Apex-Qh FTICR mass spectrometer. All compounds were analyzed for purity by HPLC using either MS or UV absorbance detectors. All the final compounds showed ≥95% purity.

Synthesis of 3-fluoro-4-hydroxy-N-(4-(4-methylpiperazin-1-yl)phenyl)benzamide: In a 25-mL round bottomed flask equipped with a nitrogen inlet and a magnetic stir bar, 200 mg (1.28 mmol) of 3-fluoro-4-hydroxybenzoic acid was added. Thionyl chloride (2 ml, 27.32 mmol) was slowly added to the reaction. The mixture was then stirred at 110° C. for 2 h before additional thionyl chloride (1 ml, 13.66 mmol) was added. The reaction mixture was stirred at reflux overnight. Excess thionyl chloride was co-evaporated with toluene to give 225 mg (100%) of the desired product. The crude product was used in the next step. 4-(4-Methylpiperazin-1-yl) aniline (245 mg, 1.28 mmol) and Et$_3$N (131 mg, 1.29 mmol) in CH$_2$Cl$_2$ (5 mL) were added to a flask containing 225 mg (1.28 mmol) 3-fluoro-4-hydroxybenzoyl chloride. The mixture was then stirred at room temperature for overnight. To the reaction mixture, 10 mL water was added and the resulting green precipitate was filtered. The precipitate was dried in vacuo to give 253 mg (60%) of the desired product as dark green solid. $^1$H NMR (400 MHz, Chloroform-d) δ 8.36 (s, 1H), 7.64 (s, 1H), 7.09 (d, J=8.5 Hz, 1H), 6.62 (d, J=8.5 Hz, 2H), 5.20 (s, 2H), 4.32 (bs, 4H), 2.54 (t, J=5.1 Hz, 4H), 2.34 (d, J=0.7 Hz, 3H). HPLC-MS: Expected: 330 (MH+); Found: 330.

Synthesis of 3-fluoro-N-(4-(4-methylpiperazin-1-yl)phenyl)-4-(2-(piperidin-1-yl)ethoxy)benzamide: In a round bottomed flask equipped with a nitrogen inlet and a magnetic stir bar, potassium carbonate (254 mg, 1.84 mmol), 3-fluoro-4-hydroxy-N-(4-(4-methylpiperazin-1-yl)phenyl)benzamide 3 (200 mg, 0.62 mmol), potassium iodide (10 mg, 0.06 mmol), acetonitrile (5 mL). The mixture was stirred for 30 minutes before 4-(2-chloroethyl)-piperidine hydrochloride (112 mg, 0.61 mmol) was added. The mixture was then stirred at reflux temperature overnight. The grey color precipitate formed was filtered, washed with water and then dried in vacuo. HPLC showed that 10% of 3-fluoro-4-hydroxy-N-(4-(4-methylpiperazin-1-yl)phenyl)benzamide was still present in the reaction. To the reaction, potassium carbonate (38.10 mg, 0.28 mmol), potassium iodide (1.5 mg, 0.006 mmol), acetonitrile (5 mL) and 4-(2-chloroethyl) piperidine hydrochloride (16.8 mg, 0.09 mmol) was added. The mixture was then stirred at reflux temperature for overnight. The grey color precipitate formed was filtered, washed with water and then dried in vacuo yielding 151 mg (55%) of the product. The grey solid was purified using polar reserve phase HPLC to yield 51 mg (6%) of the pure 3-fluoro-N-(4-(4-methylpiperazin-1-yl)phenyl)-4-(2-(piperidin-1-yl)ethoxy)benzamide as a formate salt. $^1$H NMR (400 MHz, DMSO-d6) δ 9.55 (s, 1H, NH$^+$), 8.51 (s, 1H, HCOO$^-$), 7.61 (d, J=9.1 Hz, 2H), 7.50 (dd, J=13.5, 2.3 Hz, 1H), 7.45 (dd, J=8.6, 2.3 Hz, 1H), 6.93 (d, J=9.2 Hz, 2H), 6.55 (t, J=8.6 Hz, 1H), 3.71-3.31 (m, 10H), 3.16 (s, 3H), 2.67 (t, J=5.9 Hz, 2H), 2.44-2.32 (m, 4H), 1.53-1.40 (m, 4H), 1.41-1.26 (m, 2H). $^{13}$C NMR (101 MHz, DMSO-d6) δ 165.58, 164.95, 145.33, 133.46, 125.42, 121.46, 119.14, 116.27, 114.78 (d, J=21.2 Hz), 59.89, 59.17, 54.21, 51.81, 46.82, 42.81, 25.91, 24.24. HPLC-MS: Expected: 441 (MH+); Found: 441.

Synthesis of ethyl 4-hydroxy-3-methoxybenzoate: In a round bottomed flask equipped with a nitrogen inlet and a magnetic stir bar, a solution of vanillic acid (10 g, 59.49 mmol) in EtOH (400 mL) was added. To the above solution 600 mg (6.11 mmol) of conc. H$_2$SO$_4$ was added. The mixture was then stirred at reflux temperature for 48 h. The solution was rotary evaporated. Water (100 mL) was then added to the residue and the separated greenish oil was then removed by using separatory funnel. Product was then dried in vacuo to obtain 11.45 g (98%) of ethyl 4-hydroxy-3-methoxybenzoate. $^1$H NMR (400 MHz, Chloroform-d) δ 7.62 (dd, J=8.5, 2.1 Hz, 1H), 7.53 (d, J=1.8 Hz, 1H), 6.91 (d, J=8.6 Hz, 1H), 4.33 (q, J=7.1 Hz, 2H), 3.91 (s, 3H), 1.36 (t, J=7.3 Hz, 3H). HPLC-MS: Expected: 197 (MH+); Found: 197.

Synthesis of ethyl 3-methoxy-4-((3-(trifluoromethyl)benzyl)oxy)benzoate: Into a round bottomed flask equipped with a nitrogen inlet and a magnetic stir bar, potassium carbonate (1.86 g, 13.46 mmol), ethyl 4-hydroxy-3-methoxybenzoate (1.2 g, 6.12 mmol) and CH$_3$CN (26 mL) was added. The mixture was stirred for 30 minutes before 1-(bromomethyl)-3-(trifluoromethyl)benzene (1.59 g, 6.65 mmol) was added. The mixture was then stirred at reflux temperature overnight. The reaction mixture was rotary evaporated. Water (100 mL) was then added to the residue and the aqueous was then extracted with EtOAc (3×50 mL). The combined organic layers were evaporated and then dried in vacuo yielding 2.08 g (96%) of ethyl 3-methoxy-4-((3-(trifluoromethyl)benzyl)oxy)benzoate as beige solid. $^1$H NMR (400 MHz, Chloroform-d) δ 7.69 (s, 1H), 7.63 (d, J=2.0 Hz, 1H), 7.60 (d, J=2.0 Hz, 1H), 7.57 (d, J=2.0 Hz, 1H), 7.56 (s, 1H), 7.48 (t, J=7.7 Hz, 1H), 6.87 (d, J=8.4 Hz, 1H), 5.22 (s, 2H), 4.34 (q, J=7.1 Hz, 2H), 3.93 (s, 3H), 1.36 (t, J=7.1 Hz, 3H). HPLC-MS: Expected: 355 (MH+); Found: 355.

Synthesis of ethyl 4-((4-cyanobenzyl)oxy)-3-methoxybenzoate: Ethyl 4-((4-cyanobenzyl)oxy)-3-methoxybenzoate was synthesized using procedure similar to ethyl 3-methoxy-4-((3-(trifluoromethyl)benzyl)oxy)benzoate to yield 2.04 g (49%) as a beige solid. $^1$H NMR (400 MHz, Chloroform-d) δ 7.80-7.35 (m, 6H), 6.82 (d, J=8.4 Hz, 1H), 5.24 (s, 2H), 4.34 (q, J=7.1 Hz, 2H), 3.93 (s, 3H), 1.36 (t, J=7.1 Hz, 3H).

Synthesis of ethyl 3-methoxy-4-((4-(trifluoromethoxy)benzyl)oxy)benzoate: Ethyl 3-methoxy-4-((4-(trifluoromethoxy)benzyl)oxy)benzoate was synthesized using procedure similar to ethyl 3-methoxy-4-((3-(trifluoromethyl)benzyl)oxy) benzoate to yield 2.26 g as a beige solid. $^1$H NMR (400 MHz, Chloroform-d) δ 7.61 (ddd, J=8.4, 2.0, 0.8 Hz, 1H), 7.56 (s, 1H), 7.45 (d, J=8.9 Hz, 2H), 7.21 (d, J=8.1 Hz, 2H), 6.86 (d, J=8.4 Hz, 1H), 4.33 (q, J=7.4 Hz, 1H), 3.92 (s, 7H), 1.36 (t, J=7.1 Hz, 1H).

Synthesis of 3-methoxy-4-((3-(trifluoromethyl)benzyl)oxy)benzoic acid: Into a round bottomed flask equipped with a nitrogen inlet and a magnetic stir bar, a solution of ethyl 3-methoxy-4-((3-(trifluoromethyl)benzyl)oxy)benzoate (2.08 g, 5.88 mmol) in MeOH (28 mL) was added. To the above, 8 mL of 5% NaOH solution was added. The reaction mixture was stirred at room temperature for overnight. The mixture was rotary evaporated and 20 mL of cold water was added. The aqueous was acidified with 6 N HCl. The precipitate was filtered and the solid, washed with 5 mL of water and then dried in vacuo to give 1.67 g (87%) of the white color solid as pure 3-methoxy-4-((3-(trifluoromethyl)-benzyl)oxy)benzoic acid. $^1$H NMR (400 MHz, Methanol-d4) δ 7.77 (s, 1H), 7.71 (d, J=6.7 Hz, 1H), 7.69-7.47 (m, 4H), 7.07 (dd, J=8.4, 2.7 Hz, 1H), 5.24 (s, 2H), 3.88 (s, 3H).

Synthesis of 4-((4-cyanobenzyl)oxy)-3-methoxybenzoic acid: 4-((4-Cyanobenzyl)oxy)-3-methoxybenzoic acid was synthesized using procedure similar to 3-methoxy-4-((3-(trifluoromethyl)-benzyl)oxy)benzoic acid to get 1.28 g (74%) of the white color solid as pure and desired product. $^1$H NMR (400 MHz, Chloroform-d) δ 7.65 (dt, J=6.3, 1.4 Hz, 2H), 7.61-7.56 (m, 1H), 7.56-7.50 (m, 3H), 7.24 (t, J=1.7 Hz, 1H), 5.22 (s, 2H), 3.92 (s, 3H). HPLC-MS (negative mode): Expected: 282 (M-1); Found: 282.

Synthesis of 3-methoxy-4-((4-(trifluoromethoxy)benzyl)oxy)benzoic acid: 3-Methoxy-4-((4-(trifluoromethoxy)benzyl)oxy)benzoic acid was synthesized using procedure similar to 3-methoxy-4-((3-(trifluoromethyl)-benzyl)oxy) benzoic acid to get 2.096 g (100%) of the white color solid as pure and desired product. $^1$H NMR (400 MHz, Chloroform-d) δ 7.58 (dd, J=15.1, 1.9 Hz, 2H), 7.45 (d, J=8.7 Hz, 2H), 7.21 (d, J=8.6 Hz, 2H), 6.87 (d, J=8.5 Hz, 1H), 5.17 (s, 2H), 3.87 (s, 3H). HPLC-MS (negative mode): Expected: 341 (M-1); Found: 341.

Synthesis of 3-methoxy-4-((3-(trifluoromethyl)benzyl)oxy)benzoyl chloride: In a 25-mL round bottomed flask containing 300 mg (0.83 mmol) of 3-methoxy-4-((3-(trifluoromethyl)benzyl)oxy)benzoic acid, thionyl chloride (1.5 ml, 20.68 mmol) was added. The mixture was stirred at 110° C. for 2 h before additional thionyl chloride (1.0 ml, 13.78 mmol) was added. The reaction mixture was stirred at reflux overnight. Excess thionyl chloride was co-evaporated with toluene to give 292 mg (>100%) of 3-methoxy-4-((3-(trifluoromethyl)benzyl)oxy)benzoyl chloride. The compound was used in the next step.

Synthesis of 4-((4-cyanobenzyl)oxy)-3-methoxybenzoyl chloride: 4-((4-Cyanobenzyl)oxy)-3-methoxybenzoyl chloride was synthesized using procedure similar to 3-methoxy-4-((3-(trifluoromethyl)benzyl)oxy)benzoyl chloride to obtain 451 mg (85%) of the desired product as beige solid. $^1$H NMR (400 MHz, Chloroform-d) δ 7.75 (d, J=8.5 Hz, 1H), 7.66 (t, J=7.9 Hz, 2H), 7.55 (s, 2H), 7.53 (s, 1H), 6.85 (dd, J=22.7, 8.6 Hz, 1H), 5.26 (s, 2H), 3.93 (s, 3H).

Synthesis of 3-methoxy-4-((4-(trifluoromethoxy)benzyl)oxy)benzoyl chloride: 3-Methoxy-4-((4-(trifluoromethoxy)benzyl)oxy)benzoyl chloride was synthesized using procedure similar to 3-methoxy-4-((3-(trifluoromethyl)benzyl)oxy)benzoyl chloride 463 mg (78%) of the desired product as beige solid. The compound was used in the next step.

Synthesis of 3-methoxy-N-(4-(4-methylpiperazin-1-yl)phenyl)-4-((4-(trifluoromethoxy)benzyl)oxy)benzamide: In a round bottomed flask equipped with a nitrogen inlet and a magnetic stir bar, 3-methoxy-4-((4-(trifluoromethoxy)benzyl)oxy)benzoyl chloride (147 mg, 0.41 mmol), 4-(4-methylpiperazin-1-yl)aniline (78 mg, 0.41 mmol) and Et$_3$N (0.13 mL, 0.93 mmol) in CH$_2$Cl$_2$ (5 mL) were added. The mixture was then stirred at room temperature for overnight. The mixture was filtered and the light gray solid was washed with CH$_2$Cl$_2$ and then dried in vacuo to give 17 mg (8%) of pure 3-methoxy-N-(4-(4-methylpiperazin-1-yl)phenyl)-4-((4-(trifluoromethoxy)benzyl)oxy)benzamide. $^1$H NMR (400 MHz, DMSO-d6) δ 9.88 (s, 1H), 7.65-7.43 (m, 6H), 7.38 (d, J=8.2 Hz, 2H), 7.11 (d, J=8.6 Hz, 1H), 6.88 (d, J=9.0 Hz, 2H), 5.18 (s, 2H), 3.82 (s, 3H), 3.16-2.89 (m, 4H), 2.44-2.33 (m, 4H), 2.18 (s, 3H). $^{13}$C NMR (101 MHz, DMSO-d6) δ 164.70, 150.50, 148.97, 148.35, 147.81, 136.73, 131.46, 130.43, 129.87, 128.12, 122.34, 121.81 (d, J=10.9 Hz), 121.29 (d, J=14.4 Hz), 120.77, 115.84, 112.90 (d, J=39.0 Hz), 111.66 (d, J=59.9 Hz), 69.30, 56.13 (d, J=16.7 Hz), 55.07 (t, J=30.8 Hz), 48.91, 46.21 (d, J=31.9 Hz). HPLC-MS: Expected: 516 (MH$^+$); Found: 516. HPLC-MS: Expected: 516 (MH$^+$); Found: 516.

Synthesis of 3-methoxy-N-(4-(4-methylpiperazin-1-yl)phenyl)-4-((3-(trifluoromethyl)benzyl)oxy)benzamide: In a round bottomed flask equipped with a nitrogen inlet and a magnetic stir bar, 3-methoxy-4-((3-(trifluoromethyl)benzyl)oxy)benzoyl chloride (143 mg, 0.415 mmol), 4-(4-methylpiperazin-1-yl)aniline (79.4 mg, 0.415 mmol) and Et$_3$N (0.15 mL, 1.08 mmol) in CH$_2$Cl$_2$ (5 mL) were added. The mixture was then stirred at room temperature for overnight. The crude was then filtered to give white solid. The solid white solid was washed with CH$_2$Cl$_2$, dried in vacuo to give 10 mg of the desired compound. To the filtrate, 10 mL of water was added and the aqueous was extracted with CH$_2$Cl$_2$. The organic layer was dried over Na$_2$SO$_4$, filtered, rotary evaporated. The crude was purified by preparatory TLC with 10% MeOH in CH$_2$Cl$_2$ to give 80 mg of 3-methoxy-N-(4-(4-methylpiperazin-1-yl)phenyl)-4-((3-(trifluoromethyl)benzyl)oxy)benzamide. Over all yield is 90 mg (39%). $^1$H NMR (400 MHz, DMSO-d6) δ 9.86 (s, 1H), 7.82 (s, 1H), 7.75 (d, J=9.0 Hz, 1H), 7.69 (d, J=8.8 Hz, 1H), 7.62 (t, J=8.2 Hz, 1H), 7.58-7.45 (m, 4H), 7.14 (d, J=8.6 Hz, 1H), 6.89 (d, J=9.1 Hz, 2H), 5.26 (s, 2H), 3.83 (s, 3H), 3.15-2.95 (m, 4H), 2.48 (t, J=4.7 Hz, 4H, partially covered by DMSO NMR solvent peak), 2.21 (s, 3H). $^{13}$C NMR (101 MHz, DMSO-d6) δ 164.72, 150.47, 149.10, 147.84, 138.81, 132.25, 131.52, 130.08, 128.37, 125.93-125.06 (m), 124.64 (d, J=4.1 Hz), 122.07, 121.10, 115.92, 113.17, 111.76, 69.50, 56.20, 55.05, 48.88, 46.12. HPLC-MS: Expected: 500 (MH+); Found: 500.

Synthesis of 4-((4-cyanobenzyl)oxy)-3-methoxy-N-(4-(4-methylpiperazin-1-yl)phenyl)benzamide: 4-((4-cyanobenzyl)oxy)-3-methoxy-N-(4-(4-methylpiperazin-1-yl)phenyl) benzamide was prepared using procedure similar to Synthesis of 3-methoxy-N-(4-(4-methylpiperazin-1-yl)phenyl)-4-((3-(trifluoromethyl)benzyl)oxy)benzamide. $^1$H NMR (400 MHz, DMSO-d6) δ 9.96 (s, 1H), 7.85 (d, J=8.4 Hz, 2H), 7.67-7.57 (m, 4H), 7.57-7.50 (m, 2H), 7.09 (d, J=9.1 Hz, 1H), 6.96 (d, J=9.1 Hz, 2H), 5.27 (s, 2H), 3.84 (s, 3H), 3.80-3.50 (m, 4H), 2.75 (s, 3H), at 2.58-2.28 (bs, 4 protons from piperazine ring covered under DMSO peak). $^{13}$C NMR (101 MHz, DMSO-d6) δ 165.02, 150.30, 148.98, 146.32, 142.94, 132.86 (d, J=32.3 Hz), 132.39, 128.58 (d, J=36.7 Hz), 128.06, 122.23 (d, J=37.8 Hz), 121.15 (d, J=38.5 Hz), 119.20, 116.67, 113.03 (d, J=15.9 Hz), 111.60 (d, J=37.6 Hz), 110.92, 69.27, 56.16 (d, J=22.9 Hz), 52.91, 46.53, 42.68 (d, J=28.4 Hz). HPLC-MS: Expected: 457 (MH$^+$); Found: 457.

Synthesis of 4-((4-cyanobenzyl)oxy)-3-methoxy-N-(4-(4-methoxypiperidin-1-yl)phenyl)benzamide: In a round bottomed flask equipped with a nitrogen inlet and a magnetic stir bar, 4-((4-cyanobenzyl)oxy)-3-methoxybenzoyl chloride (142 mg, 0.47 mmol), 4-(4-methoxypiperidin-1-yl)aniline (97 mg, 0.47 mmol) and Et$_3$N (0.14 mL, 1.00 mmol) in CH$_2$Cl$_2$ (5 mL) were added. The reaction mixture was washed with H$_2$O$_2$O and the aqueous was extracted with CH$_2$Cl$_2$. The organic layer was dried over Na$_2$SO$_4$, filtered and then concentrated using rotary evaporator. To the residue 10 mL of CH$_2$Cl$_2$ and 4 mL of 3 N methanolic HCl was added and stirred at room temperature for 5 h. The reaction mixture was then concentrated and then dried in vacuo to give black solid as crude product. The product was dissolved in EtOH and grayish compound was filtered and dried in vacuo to yield 50 mg (21%) of 4-((4-cyanobenzyl)oxy)-3-methoxy-N-(4-(4-methoxypiperidin-1-yl)phenyl)-benzamide (100% HPLC purity). $^1$H NMR (400 MHz, DMSO-d6) δ 10.34 (s, 1H), 7.92-7.82 (m, 4H), 7.79-7.66 (m, 2H), 7.62 (d, J=6.7 Hz, 2H), 7.60-7.55 (m, 3H), 7.12 (d, J=9.1 Hz, 1H), 5.28 (s, 2H), 3.85 (s, 3H), 3.61-3.48 (m, 5H), 3.27 (s, 3H), 2.29-2.11 (m, 2H), 2.08-1.88 (m, 2H). $^{13}$C NMR (101 MHz, DMSO-d6) δ 165.40, 150.71, 149.10, 142.97, 133.86-131.37 (m), 128.85, 128.25, 127.67, 122.79-120.35 (m), 121.14, 119.16, 113.31, 112.83, 112.28, 111.67, 111.00, 69.31, 56.34, 56.22, 55.84, 55.53. HPLC-MS: Expected: 472 (MH$^+$); Found: 472.

Synthesis of N-(4-(4-methoxypiperidin-1-yl)phenyl) benzo[d][1,3]dioxole-5-carboxamide: In a round bottomed flask equipped with a nitrogen inlet and a magnetic stir bar, benzo[d][1,3]dioxole-5-carbonyl chloride (136 mg, 0.74 mmol), 4-(4-methoxypiperidin-1-yl)aniline (150 mg, 0.74 mmol) and Et$_3$N (0.30 mL, 2.15 mmol) in CH$_2$Cl$_2$ (5 mL) was added. The mixture was then stirred at room temperature for overnight. To the reaction 20 mL of water was added and the layers were separated. The aqueous layer was then washed with CH$_2$Cl$_2$ (2×15 mL). The combined organic solvent was then dried over Na$_2$SO$_4$, filtered, concentrated by rotary evaporation and then dried in vacuo. The crude was purified by column chromatography and the product was eluted with 35% EtOAc in hexanes to yield 41 mg (16%) of N-(4-(4-methoxypiperidin-1-yl)phenyl)benzo[d][1,3]dioxole-5-carboxamide as beige color solid. $^1$H NMR (400 MHz, CDCl$_3$) δ 7.54-7.50 (m, 3H), 7.45 (s, 1H), 7.00 (d, J=8 Hz, 1H), 6.88 (d, J=8 Hz, 2H), 6.09 (s, 2H), 3.43-3.37 (m, 2H), 3.30-3.25 (m, 1H), 3.23 (s, 3H), 2.82-2.76 (m, 2H), 1.91-1.87 (m, 2H), 1.52-1.44 (m, 2H). $^{13}$C NMR (101 MHz, DMSO-d6) δ 164.30, 150.20, 147.80, 147.73, 131.25, 129.36, 122.99, 121.89, 116.35, 108.30, 108.00 (d, J=4.5 Hz), 102.12 (t, J=6.1 Hz), 75.83, 55.26 (d, J=4.3 Hz), 47.15, 30.61. HPLC-MS: Expected: 355 (MH$^+$); Found: 355.

Synthesis of N-(4-(4-methylpiperazin-1-yl)phenyl)benzo[d][1,3]dioxole-5-carboxamide: In a round bottomed flask equipped with a nitrogen inlet and a magnetic stir bar, benzo[d][1,3]dioxole-5-carbonyl chloride (164 mg, 0.89 mmol), 4-(4-methylpiperazin-1-yl)aniline (170 mg, 0.89 mmol) and Et$_3$N (0.38 mL, 2.73 mmol) in CH$_2$Cl$_2$ (5 mL) was added. The mixture was then stirred at room temperature for overnight. The precipitate formed was then filtered, washed with CH$_2$Cl$_2$ and the residue was dried in vacuo yielding 205 mg (68%) of N-(4-(4-methylpiperazin-1-yl) phenyl)benzo[d][1,3]dioxole-5-carboxamide as blackish solid. $^1$H NMR (400 MHz, CDCl$_3$) δ 9.83 (s, 1H, NH), 7.55-7.52 (m, 3H), 7.50 (s, 1H), 7.00 (d, J=8 Hz, 1H), 6.87 (d, J=8 Hz, 2H), 6.09 (s, 2H), 3.05 (t, J=8 Hz, 4H), 2.41 (t, J=8 Hz, 4H), 3.23 (s, 3H). $^{13}$C NMR (101 MHz, DMSO-d6) δ 164.30, 150.20, 147.83, 147.73, 131.45, 129.35, 12.03, 121.87 (d, J=4.5 Hz), 115.85, 108.30, 108.00 (d, J=4.5 Hz), 102.15 (t, J=6.1 Hz), 55.07, 48.90, 46.21 (d, J=4.3 Hz). HPLC-MS: Expected: 340 (MH$^+$); Found: 340.

Synthesis of ethyl 3-fluoro-4-hydroxybenzoate: Ethyl 3-fluoro-4-hydroxybenzoate was synthesized using procedure similar to preparation of ethyl 4-hydroxy-3-methoxybenzoate to get 1.67 g (56%) of the desired product as yellow oil that turns into beige solid on storing. 1H NMR (400 MHz, Methanol-d4) δ 7.87-7.36 (m, 2H), 7.94 (t, J=7.6 Hz, 1H), 4.30 (q, J=7.4 Hz, 2H), 1.34 (t, J=7.1 Hz, 3H). HPLC-MS: Expected: 185 (MH+); Found: 185

Synthesis of ethyl 3-fluoro-4-(2-morpholinoethoxy)benzoate: Ethyl 3-fluoro-4-(2-morpholinoethoxy)benzoate was synthesized using procedure similar to preparation of ethyl 3-methoxy-4-((3-(trifluoromethyl)benzyl)oxy) benzoate to get 1.26 g (98%) of the desired product as beige solid. $^1$H NMR (400 MHz, Chloroform-d) δ 7.77 (d, J=8.5 Hz, 1H), 7.72 (d, J=11.7 Hz, 1H), 6.95 (t, J=9.1 Hz, 1H), 4.32 (q, J=7.6 Hz, 2H), 4.21 (t, J=5.7 Hz, 2H), 3.74-3.66 (m, 4H), 2.83 (t, J=5.7 Hz, 2H), 2.63-2.45 (m, 4H), 1.35 (t, J=7.1 Hz, 3H). HPLC-MS: Expected: 299 (M+1); Found: 299.

Synthesis of 3-fluoro-4-(2-morpholinoethoxy)benzoic acid: 3-Fluoro-4-(2-morpholinoethoxy)benzoic acid was synthesized using procedure similar to preparation of 3-methoxy-4-((3-(trifluoromethyl)benzyl)oxy)benzoic acid to get 1.25 g (100%) of the beige color solid as pure and desired product. $^1$H NMR (400 MHz, Methanol-d4) δ 8.51 (s, 1H), 7.70 (d, J=8.5 Hz, 1H), 7.62 (dd, J=12.4, 2.0 Hz, 1H), 7.06 (t, J=8.4 Hz, 1H), 4.23 (t, J=5.4 Hz, 2H), 3.70-3.64 (m, 2H), 2.83 (t, J=5.4 Hz, 2H), 2.67-2.56 (m, 4H), 2.51 (t, J=6.0 Hz, 2H). HPLC-MS: Expected: 270 (MH+); Found: 270.

Synthesis of 3-fluoro-N-(4-(4-methylpiperazin-1-yl)phenyl)-4-(2-morpholinoethoxy)benzamide: In a round bottomed flask equipped with a magnetic stir bar and a nitrogen inlet, a mixture of 3-fluoro-4-(2-morpholinoethoxy)benzoic acid (135 mg, 0.05 mmol), HATU (494 mg, 1.3 mmol) and DIPEA (0.1 mL, 0.73 mmol) in 3 mL DMF was added. The mixture was then stirred at room temperature for one hour. To the above solution, 4-(4-methylpiperazin-1-yl)aniline (95 mg, 0.50 mmol) was added. The mixture was stirred at room temperature for 16 h. To the mixture sat. aq. NaHCO$_3$ solution was added and the aqueous was extracted with CH$_2$Cl$_2$. The combined organic layers were dried over Na$_2$SO$_4$, filtered, removed by rotary evaporation and the crude was purified by preparation TLC with 10% MeOH in DCM to obtain 126 mg (57%) of pure 3-fluoro-N-(4-(4-methylpiperazin-1-yl)phenyl)-4-(2-morpholinoethoxy)benzamide. ¹H NMR (400 MHz, Chloroform-d) δ 7.62-7.54 (m, 2H), 7.46 (d, J=8.9 Hz, 2H), 6.96 (t, J=8.5 Hz, 1H), 6.87 (d, J=9.0 Hz, 2H), 4.19 (t, J=5.7 Hz, 2H), 3.69 (t, J=4.8 Hz, 4H), 3.15 (t, J=5.2 Hz, 4H), 2.81 (t, J=5.7 Hz, 2H), 2.60-2.49 (m, 8H), 2.32 (s, 3H). ¹³C NMR (101 MHz, Chloroform-d) δ 163.98, 153.32, 150.86, 149.57 (d, J=10.9 Hz), 148.42, 130.16, 128.08 (d, J=5.5 Hz), 123.50 (d, J=15.5 Hz), 121.78 (d, J=14.4 Hz), 116.49, 115.37, 114.10, 67.55 (t, J=7.3 Hz), 66.90 (t, J=15.2 Hz), 57.30 (t, J=8.6 Hz), 55.04 (t, J=11.8 Hz), 54.11 (t, J=12.9 Hz), 49.36 (t, J=3.6 Hz), 46.11 (d, J=14.2 Hz). HPLC-MS: Expected: 443 (MH⁺); Found: 443.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A composition comprising a compound capable of docking within a CRMP2 binding pocket characterized by one or more of the following CRMP2 amino acid residues: LYS23, MET64, SER322, TRP366, VAL370, VAL371, GLY373, LYS374, MET375, GLU377, GLN379, PRO414, and ARG440, wherein the compound is a small molecule having a substituted methyl-piperazine-phenyl-benzamide core.

2. The composition of claim 1, wherein the amount of the compound is a therapeutically effective amount capable of inhibiting SUMOylation of CRMP2 in a subject.

3. The composition of claim 2, wherein the composition is administered to a subject experiencing pain.

4. The composition of claim 1, wherein the CRMP2 binding pocket is characterized by the following CRMP2 amino acid residues: LYS23, MET64, SER322, TRP366, VAL370, VAL371, GLY373, LYS374, MET375, GLU377, GLN379, PRO414, and ARG440.

5. The composition of claim 1, wherein the compound is selected from the group consisting of:

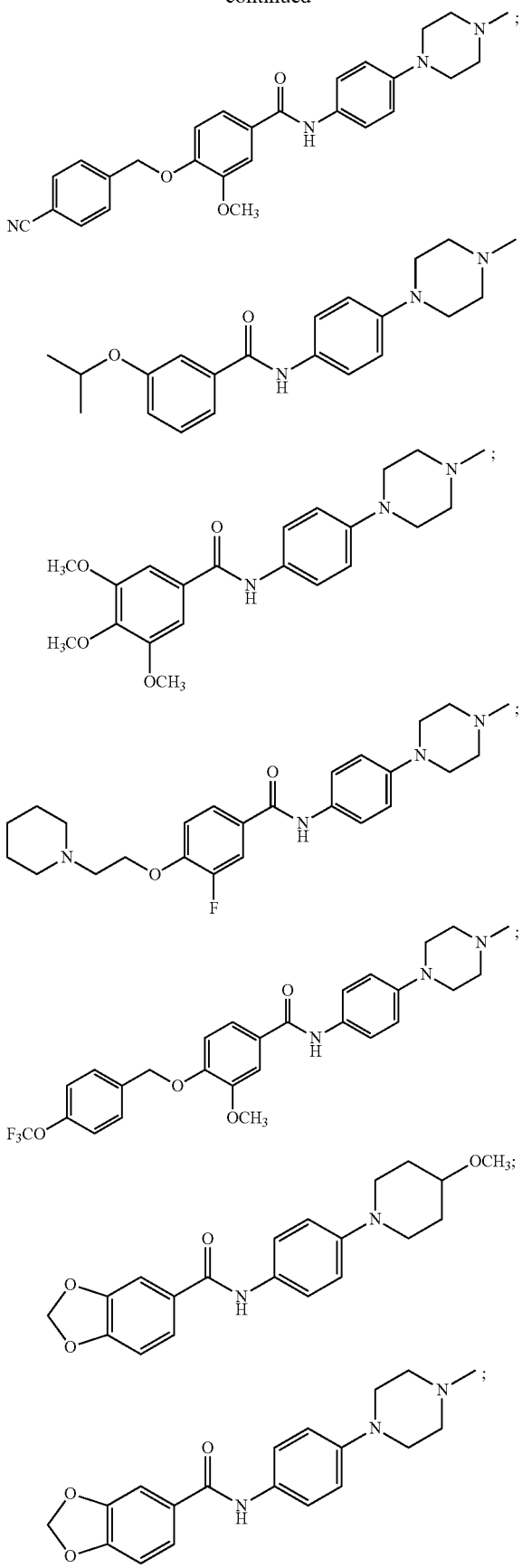

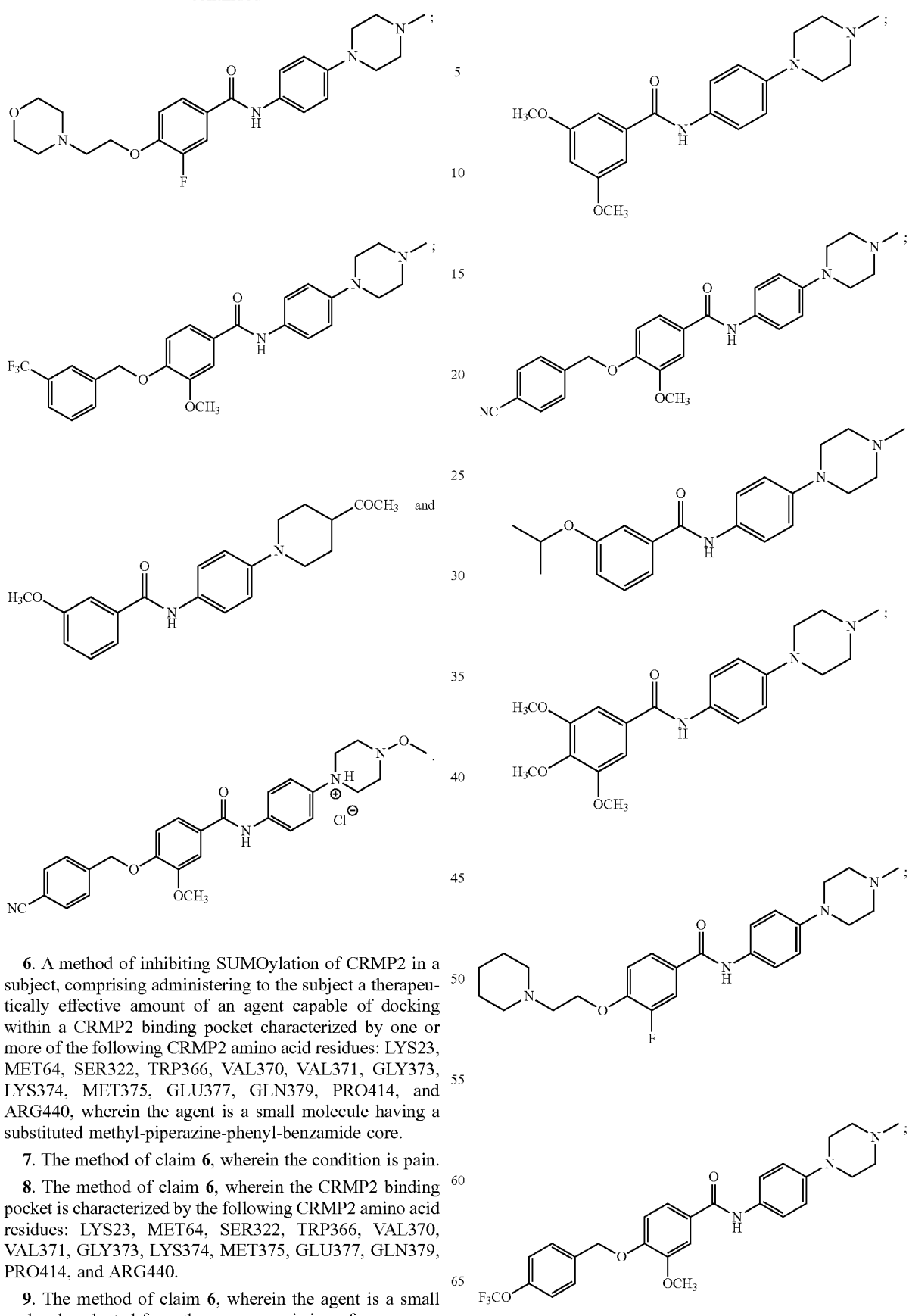

6. A method of inhibiting SUMOylation of CRMP2 in a subject, comprising administering to the subject a therapeutically effective amount of an agent capable of docking within a CRMP2 binding pocket characterized by one or more of the following CRMP2 amino acid residues: LYS23, MET64, SER322, TRP366, VAL370, VAL371, GLY373, LYS374, MET375, GLU377, GLN379, PRO414, and ARG440, wherein the agent is a small molecule having a substituted methyl-piperazine-phenyl-benzamide core.

7. The method of claim 6, wherein the condition is pain.

8. The method of claim 6, wherein the CRMP2 binding pocket is characterized by the following CRMP2 amino acid residues: LYS23, MET64, SER322, TRP366, VAL370, VAL371, GLY373, LYS374, MET375, GLU377, GLN379, PRO414, and ARG440.

9. The method of claim 6, wherein the agent is a small molecule selected from the group consisting of:

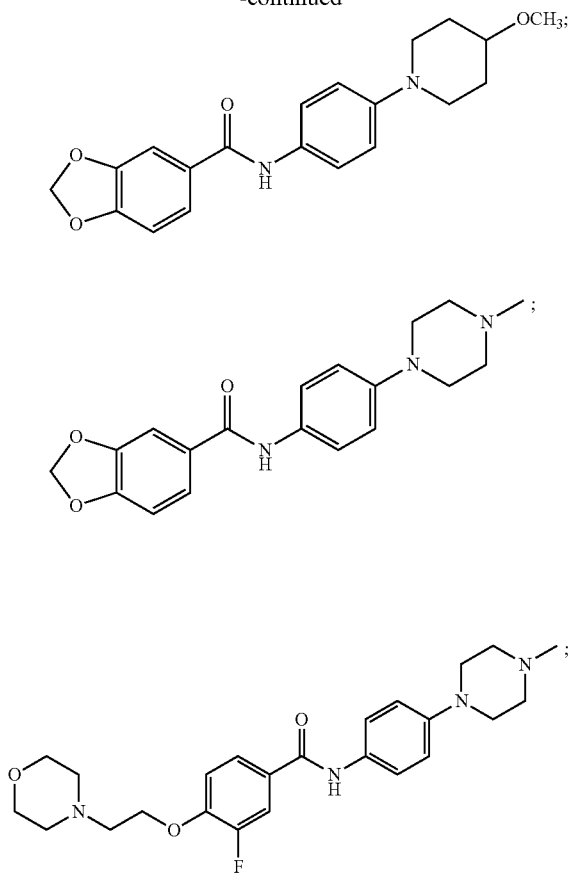
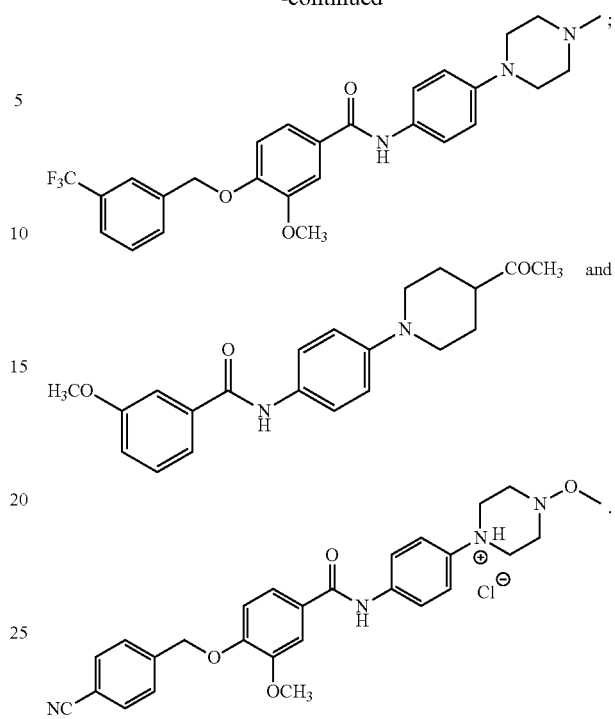
10. The method of claim 6, wherein the subject is a human patient.
11. The method of claim 10, wherein the human patient is suffering from pain related to Nav1.7 activity.
* * * * *